US 12,422,400 B2

(12) United States Patent
Bockelmann et al.

(10) Patent No.: US 12,422,400 B2
(45) Date of Patent: Sep. 23, 2025

(54) LITHOGRAPHY PRODUCTION METHOD

(71) Applicants: CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR); SORBONNE UNIVERSITE, Paris (FR)

(72) Inventors: Ulrich Bockelmann, Paris (FR); Kokoura Mensah, Paris (FR)

(73) Assignees: CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR); SORBONNE UNIVERSITE, Paris (FR)

( * ) Notice: Subject to any disclaimer, the term of this patent is extended or adjusted under 35 U.S.C. 154(b) by 936 days.

(21) Appl. No.: 17/596,991

(22) PCT Filed: Jun. 30, 2020

(86) PCT No.: PCT/EP2020/068391
§ 371 (c)(1),
(2) Date: Dec. 22, 2021

(87) PCT Pub. No.: WO2021/001363
PCT Pub. Date: Jan. 7, 2021

(65) Prior Publication Data
US 2022/0244217 A1    Aug. 4, 2022

(30) Foreign Application Priority Data
Jul. 2, 2019   (FR) ..................... 1907342

(51) Int. Cl.
*G01N 27/414*   (2006.01)
*H01L 21/027*   (2006.01)

(52) U.S. Cl.
CPC ..... *G01N 27/4145* (2013.01); *H01L 21/0274* (2013.01)

(58) Field of Classification Search
CPC ................. G01N 27/4145; H01L 21/0274
See application file for complete search history.

(56) References Cited

U.S. PATENT DOCUMENTS 9,276,524 B2 *  3/2016  Jenkins ............. H10D 62/882
10,871,466 B2 * 12/2020  Mackin ................. G03F 7/30
(Continued)

FOREIGN PATENT DOCUMENTS

JP    H0627635 A     2/1994
WO   2011018774 A1   2/2011

OTHER PUBLICATIONS

International Search Report and Written Opinion received for PCT/EP2020/068391, mailed Dec. 15, 2020.
(Continued)

Primary Examiner — Benjamin Tzu-Hung Liu
(74) Attorney, Agent, or Firm — Greer, Burns & Crain, Ltd

(57) ABSTRACT

A method for producing a device including a deposition of a first resin layer of lithography above or on a protective layer such that the protective layer is included between a conductive layer and the first resin layer; a first lithography of the first resin layer, the protective layer and the conductive layer; preserving, in at least one preserving area of the first lithography, the superposition of the first resin layer, the protective layer and the conductive layer, and depositing, at least on the at least one preserving area of the first lithography, a second resin layer of lithography without removing (Continued)

the first resin layer; a second lithography of the second resin and the first resin, in particular for the production of electrodes. One of the possible aims is to obtain a device without introducing an impurity into the conductive layer.

12 Claims, 11 Drawing Sheets

(56) References Cited

U.S. PATENT DOCUMENTS

| | | | |
|---|---|---|---|
| 2015/0123080 A1* | 5/2015 | Yamaguchi | H01L 21/02664 257/29 |
| 2016/0013294 A1 | 1/2016 | Hou et al. | |
| 2018/0315750 A1 | 11/2018 | Hoffman | |

OTHER PUBLICATIONS

French Search Report received for Application No. 1907342, dated Mar. 17, 2020.

Blin, A., et al., "Electronic hybridization detection in microarray format and DNA genotyping," Science Reports, vol. 4, No. 4194, 2014, includes Supplement, 19 pages.

Fritz, J., et al., "Electronic detection of DNA by its intrinsic molecular charge," PNAS, vol. 99, No. 22, 2002, pp. 14142-14146.

Gentil, C., et al., "Signal enhancement in electronic detection of DNA hybridization," Physical Review E, vol. 75, No. 1, 2007, pp. 011926-1-011926-4.

Malpartida-Cardenas, K., et al., "Quantitative and rapid Plasmodium falciparum malaria diagnosis and artemisinin-resistance detection using a CMOS Lab-on-Chip platform," Biosens. Bioelectron, vol. 11, No. 145, 2019, 11 pages.

Perréard, C., et al., "Threshold voltage drift of FET sensor arrays with different gate insulators," Sensors and Actuators B: Chemical, No. 185, 2013, pp. 282-286, includes Appendix.

Pouthas, F., et al., "Spatially resolved electronic detection of biopolymers," Physical Review E, vol. 70, 2004, pp. 031906-1-031906-8.

* cited by examiner

[Fig. 4]
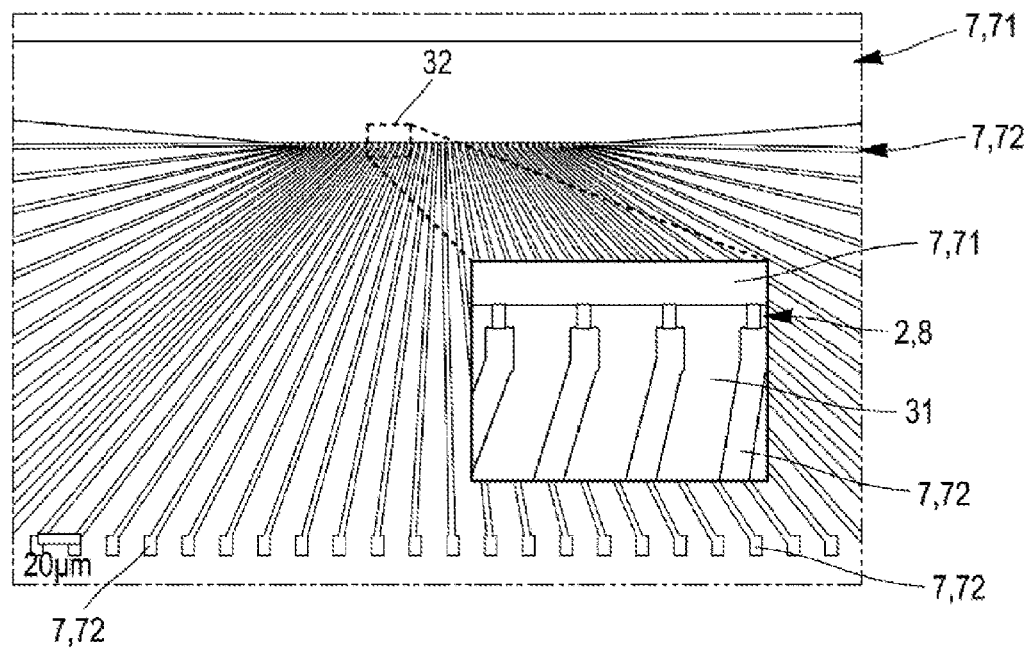
[Fig. 5]
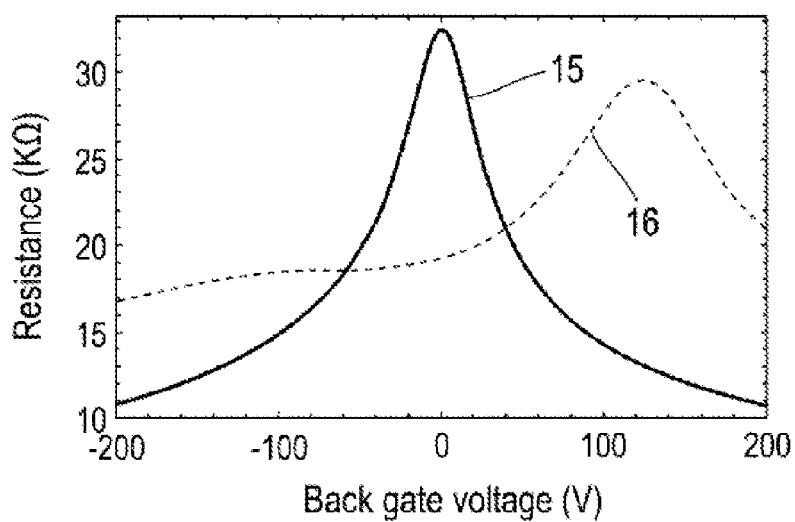

[Fig. 6]
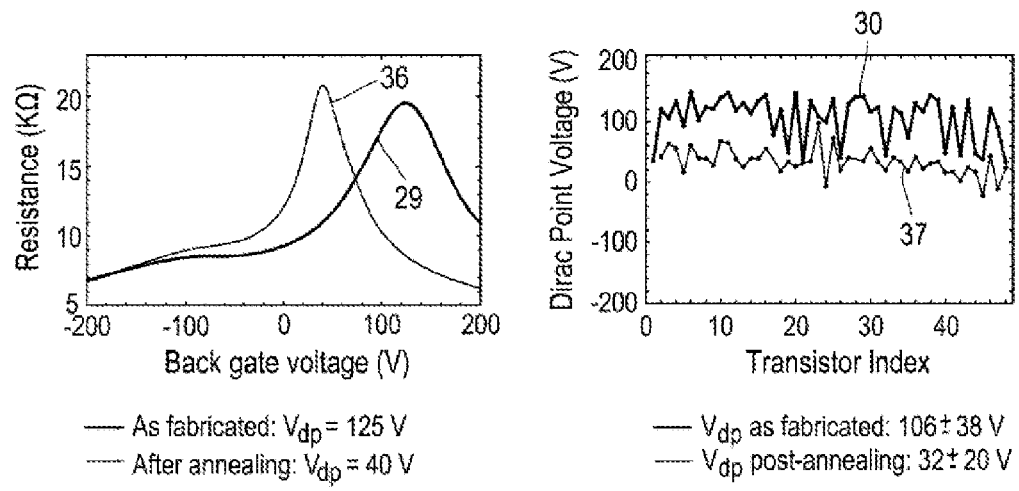
[Fig. 7]
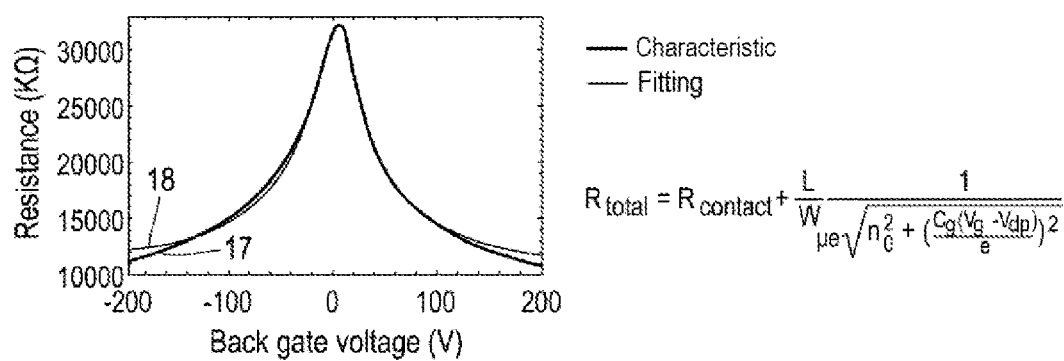

[Fig. 8]
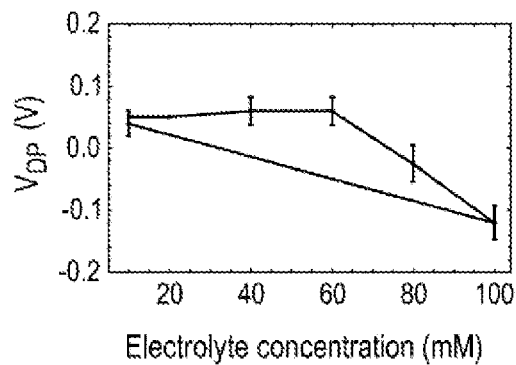
FIG. 8a
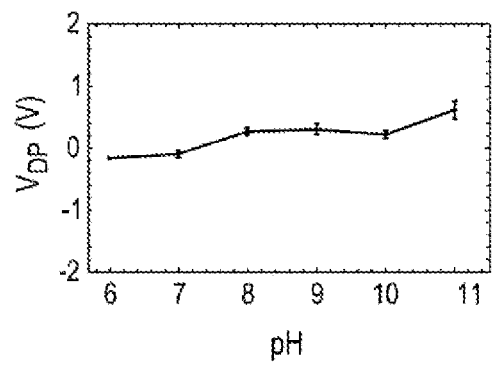
FIG. 8b
[Fig. 9]
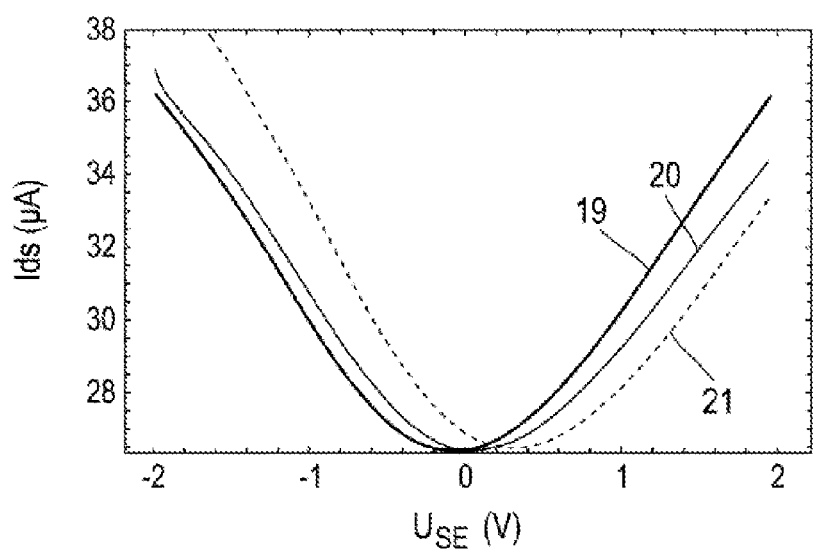
19: —— Reference
20: —— PLL: $C_0/2$
21: ---- PLL: $C_0$

[Fig. 10]
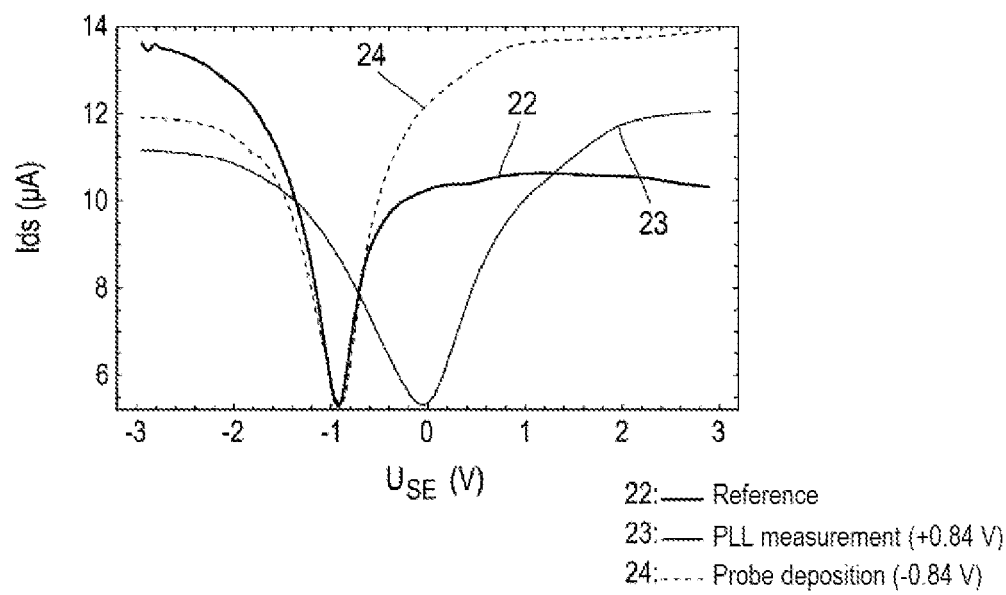
22: —— Reference
23: —— PLL measurement (+0.84 V)
24: ---- Probe deposition (-0.84 V)
[Fig. 11]
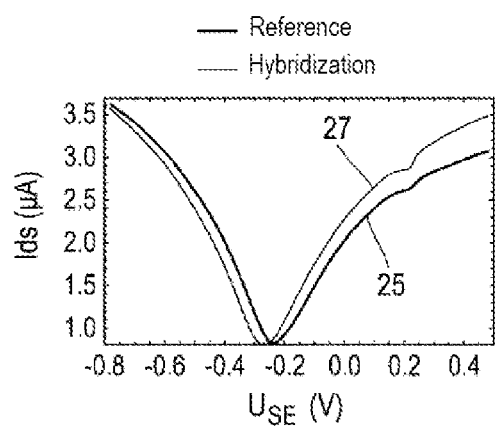 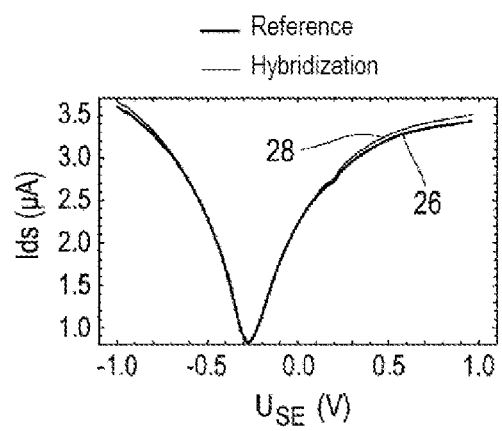
FIG. 11a　　　　　　　FIG. 11b

[Fig. 12]
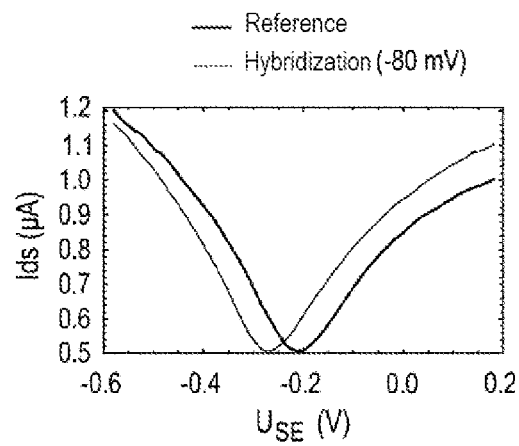
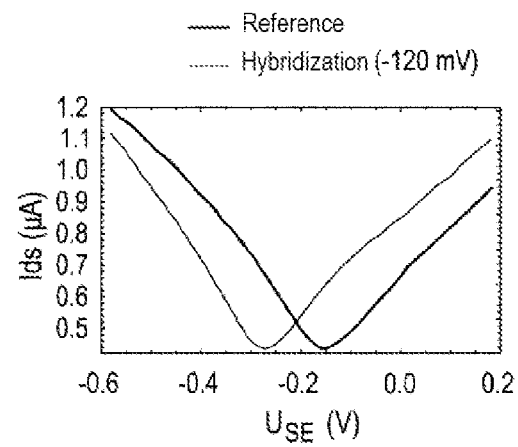
FIG. 12a    FIG. 12b
[Fig. 13]
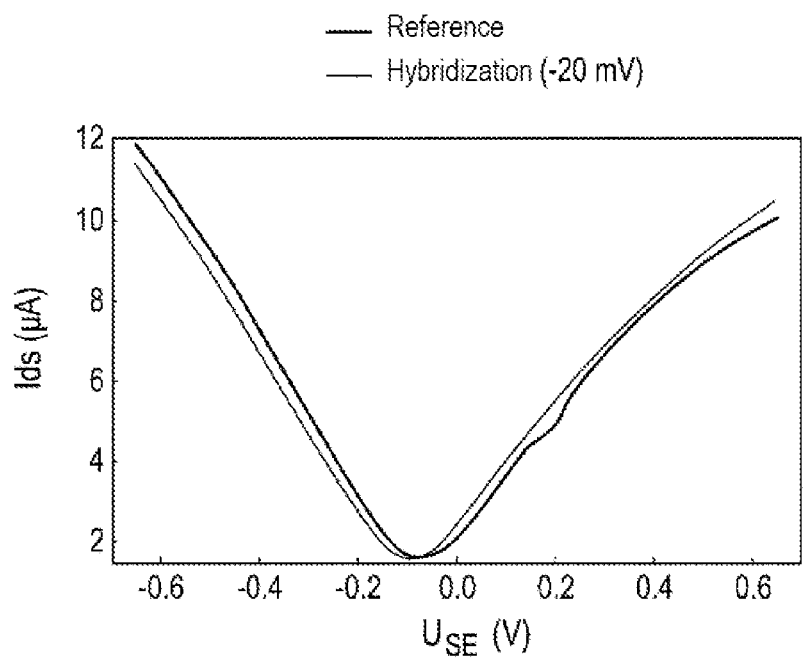

[Fig. 14]
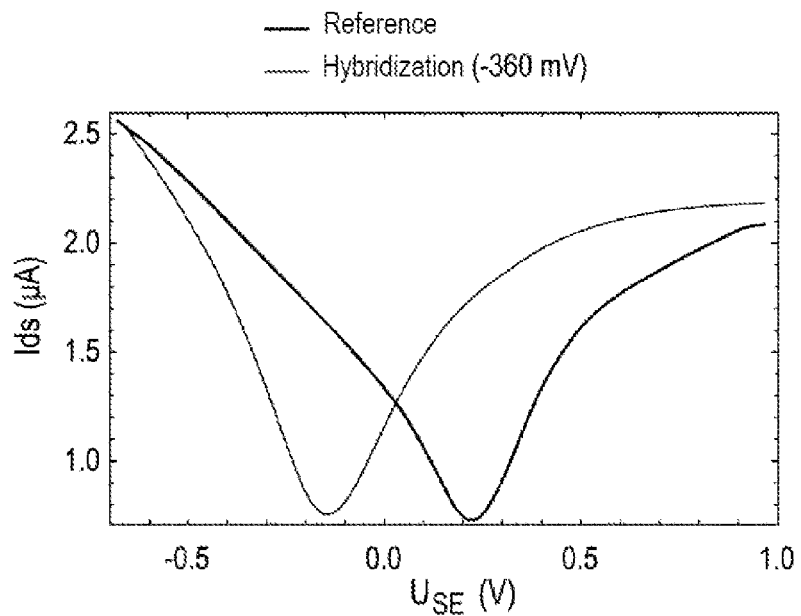
[Fig. 15]
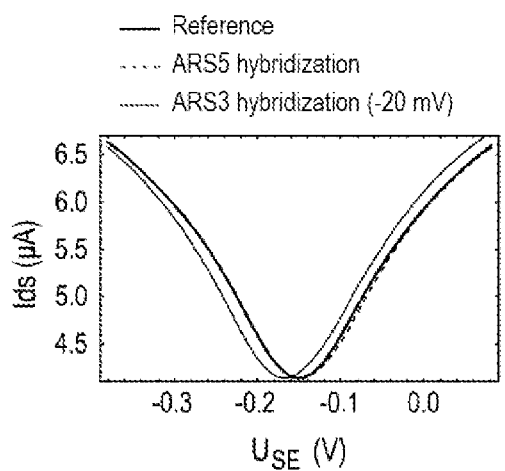
FIG. 15a
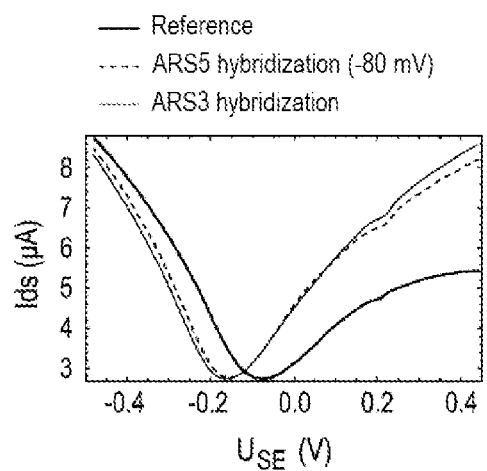
FIG. 15b

[Fig. 18]
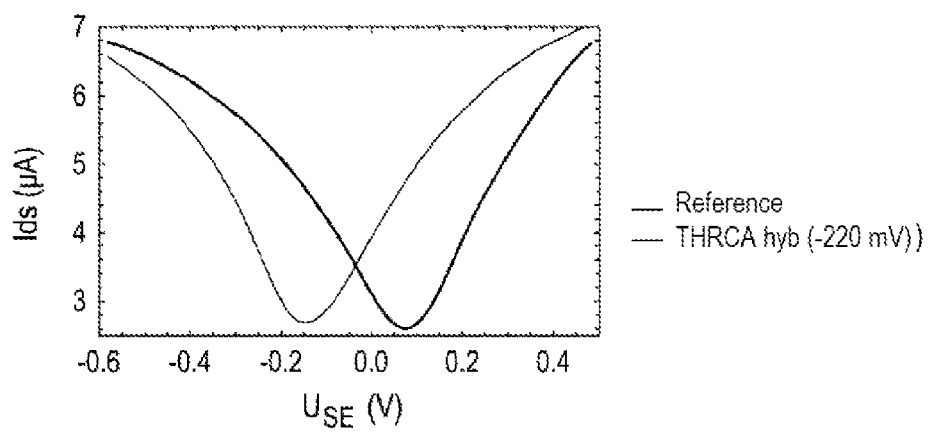
[Fig. 19]
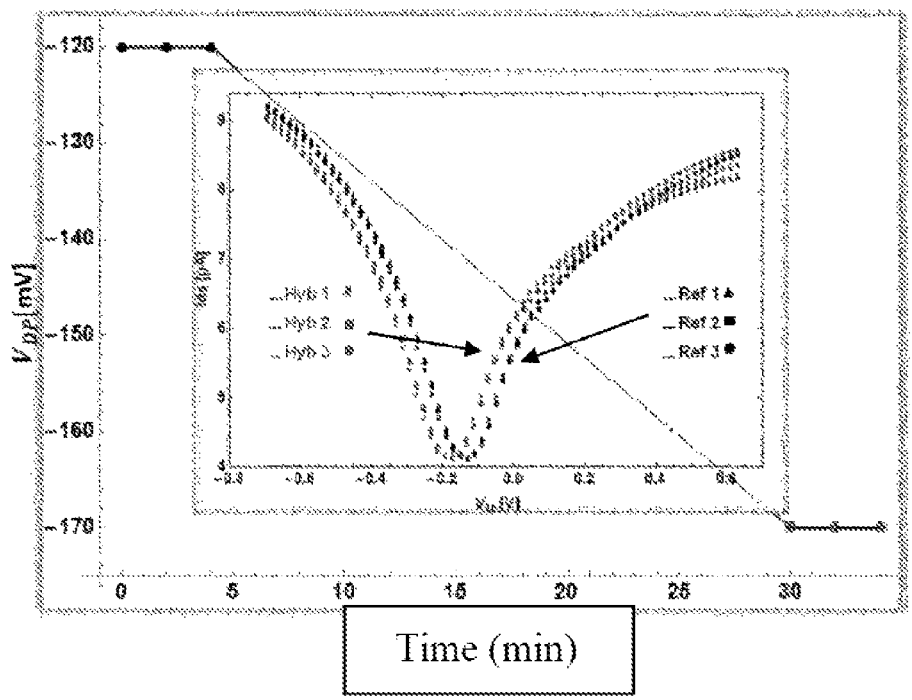

LITHOGRAPHY PRODUCTION METHOD

BACKGROUND

The present invention relates to a lithography production method. It also relates to a device produced by means of such a method, and a method for using such a device.

Such a production method makes it possible for a user to produce a device comprising a conductive layer. The field of the invention is more particularly, but non-limitatively, that of transistors or biosensors comprising a two-dimensional conductor such as graphene.

The year 2004 witnessed the birth of a new allotrope of carbon: graphene. In fact, it was in that year that the team of Geim and Novoselov succeeded in isolating a single layer of graphitic carbon for the first time by mechanical exfoliation of graphite. The synthesis of this material constituted a major event as, since 1966 (Mermin-Wagner theorem), it was believed that the existence of a two-dimensional crystal at a non-zero temperature was impossible.

Graphene has extraordinary physical properties, such as very high mobility of the charge carriers ($\mu$>100,000 cm$^2$·V$^{-1}$·s$^{-1}$ in the case of suspended graphene), a high thermal conductivity (estimated at 50 W·cm$^{-1}$·K$^{-1}$), a very high mechanical strength (rigidity constant k=50 eV·A$^{-2}$ and Young's modulus of approximately 1 TPa). Furthermore, graphene is optically transparent and absorbs only 2% of white light.

For applications in electronics and biomolecule detection, it is important to prepare a homogeneous layer with a surface area sufficient to structure it into devices. Of the methods for producing graphene, the vapour phase growth method CVD (Chemical Vapour Deposition) makes it possible to have a wide surface area of monolayer graphene. Mechanical exfoliation is currently used in research; this approach also makes it possible to have a good-quality graphene which is, however, limited to very small pieces. Whatever the preparation technique, graphene remains very sensitive to its immediate environment.

In order to produce high-performance transistors and biosensors, it is important that the graphene is not doped, i.e. has a Dirac point close to zero volts. Doping of graphene is typically caused by the introduction of organic products or the adsorption of other impurities into the graphene during the process of producing the biosensor and/or during the use of the biosensor when it is exposed to an electrolyte. The mobility of the charge carriers of graphene is reduced by the diffusion of these defects. The sensitivity of a biomolecule detection using the field effect is maximal when the graphene is intrinsic (not doped). In this detection the control of the working point of the device is performed through an electrolyte. This leads to limitations of the measurement voltage range. In fact, beyond [−1V,1V], electrochemical effects are observed at the interface between the passivation layer and the electrolyte. The degradation of this layer leads to is unreproducible measurements and uncontrolled drifts. As a result, it is important that the Dirac point of the device is located close to a zero voltage.

The aim of the present invention is to propose a method for producing a device comprising a conductive layer that has a higher performance compared with the state of the art.

Another aim is to provide a device comprising a higher-performance conductive layer.

Another aim is to provide a method for using such a device.

SUMMARY

This objective is achieved with a method for producing a device comprising:

providing a conductive layer between a substrate and a protective layer, depositing a first lithography resin layer above or on the protective layer such that the protective layer is comprised between the conductive layer and the first resin layer, a first lithography comprising:
a) removing, in at least one removal area of the first lithography, the superimposition of the first resin layer, the protective layer and the conductive layer, and
b) preserving, in at least one preservation area of the first lithography, the superimposition of the first resin layer, the protective layer and the conductive layer, and depositing, at least on the at least one preservation area of the first lithography, preferably on the at least one removal area and on the at least one preservation area of the first lithography, a second lithography resin layer without removing the first resin layer of the at least one preservation area of the first lithography, and a second lithography comprising:
a) removing, in at least one removal area of the second lithography, the superimposition of the second resin, the first resin and the protective layer, but not the conductive layer, and
b) preserving, in at least one preservation area of the second lithography, the superimposition of the second resin, the first resin, the protective layer and the conductive layer.

Preferably, the conductive layer comprises or consists of a two-dimensional conductor having a mobility greater than or equal to 1,000 cm$^2$·V$^{-1}$s$^{-1}$, preferably consisting of a layer of graphene, of silicene, of molybdenum disulfite (MoS$_2$), of germanene, of phosphorene, of stanene, or of borophene.

Preferably, the first lithography is a positive or negative lithography and the second lithography is a negative or positive lithography respectively, the first resin layer and the second resin layer being constituted by one and the same resin compatible for a positive lithography and for a negative lithography.

Preferably, the resin of the first resin layer and the resin of the second resin layer are arranged to react, during a lithography step, to the same developer and/or to the same duration, power and wavelength of a preferably ultraviolet radiation.

Preferably, the substrate comprises or consists of silicon and/or silicon oxide.

Preferably, the protective layer comprises or consists of oxidized aluminium, preferably alumina Al$_2$O$_3$.

Preferably, the production method according to the invention moreover comprises, in the at least one removal area of the second lithography, depositing at least one electrode in electrical contact with the conductive layer.

Preferably, the production method according to the invention moreover comprises, after the deposition of the at least one electrode, removing, in the at least one preservation area of the second lithography, the superimposition of the second resin and the first resin (and optionally the protective layer), but not the conductive layer. Preferably, the production method according to the invention moreover comprises, after this removal, depositing a passivation layer in contact with the conductive layer of the at least one preservation area of the second lithography and in contact with at least part of each electrode.

Preferably, the passivation layer comprises a superimposition of two different materials.

Preferably, the passivation layer comprises a superimposition:
of $Al_2O_3$ in contact with the conductive layer, then
silicon oxide in contact with the $Al_2O_3$ of the passivation layer, such that the $Al_2O_3$ of the passivation layer is comprised between the conductive layer and the silicon oxide of the passivation layer.

Preferably, the passivation layer has a breakdown field greater than or equal to $10^6$ V·m$^{-1}$.

According to yet another aspect of the invention, a device is proposed, preferably obtained by means of a production method according to the invention, and/or comprising:
a substrate,
a conductive layer divided into at least one measurement area,
at least two distinct electrodes in contact with the conductive layer characterized in that:
the conductive layer consists of a layer of a two-dimensional conductor having a doping level lower than $10^{11}$ impurities (preferably charged impurities) per cm$^2$, and/or a shift of the Dirac point with respect to 0 volts smaller than 1 volt in absolute terms, and/or
it moreover comprises a passivation layer having a breakdown field greater than or equal to $10^6$ V·m$^{-1}$ and covering the conductive layer and at least part of each electrode, such that the conductive layer and at least part of each electrode are located between the substrate and the passivation layer.

Preferably, the conductive layer is divided into several distinct measurement areas.

Preferably, the electrodes comprise a common source in contact with all the measurement areas and one drain per measurement area, each drain being in contact with only a single measurement area.

Preferably, the device according to the invention moreover comprises a tank arranged to receive an electrolyte above the conductive layer, preferably such that the electrolyte is in contact with the passivation layer or with the conductive layer.

Preferably, the device according to the invention comprises means for measuring and/or imposing a voltage and/or an electric intensity between the electrolyte and a source electrode.

Preferably, the device according to the invention comprises means for measuring and/or imposing a voltage and/or an electric intensity between a gate and a source electrode. The gate can typically comprise the substrate or an electrode produced on the measurement area or on each measurement area of the conductive layer.

Preferably, the device according to the invention comprises means for measuring and/or imposing a voltage and/or an electric intensity between a source electrode and a drain electrode.

Preferably, the device according to the invention comprises a layer of polymer and/or nucleotides above the at least one measurement area, in contact with the conductive layer or in contact with the passivation layer.

According to yet another aspect of the invention, a method for using a device according to the invention or obtained by means of a production method according to the invention is proposed, comprising:
a step of detecting the attachment of atoms or molecules (or even of biological cells) on or above the conductive layer or the passivation layer, and/or a step of detecting an electrical activity of at least one biological cell, such as for example at least one neuron, on or above the conductive layer or the passivation layer.

Preferably, the attachment is an attachment of atoms or molecules (or even of biological cells) to a layer of polymer and/or of nucleotides attached to the conductive layer or to the passivation layer.

By nucleotide is preferably meant a chain of nucleotides and/or a nucleic acid, for example DNA (deoxyribonucleic acid) or RNA (ribonucleic acid) or PNA (peptide nucleic acid).

Preferably, the attachment is a hybridization of nucleotides on a layer of polymer and nucleotides located above the at least one measurement area, and in contact with the conductive layer or in contact with the passivation layer.

BRIEF DESCRIPTION OF THE DRAWINGS

Other advantages and particular features of the invention will become apparent on reading the detailed description of implementations and embodiments that are in no way limitative, and the following attached drawings:

FIG. 4 is a photograph from above of the device 1 with an enlargement 31 of its central area 32, FIG. 5 illustrates the back gate voltage dependence on the resistance of a sheet of monolayer graphene 2 in the device 1 according to the invention (curve 15) and in another device from outside the scope of the present invention (curve 16), FIG. 6 illustrates a measurement before (curve 29) and after (curve 36) the annealing of an individual transistor on the left and a measurement before (curve 30) and after (curve 37) the annealing of all of the network of transistors on the right, in another device from outside the scope of the present invention, FIG. 7 illustrates the experimental data (curve 17) and the theoretical formula (curve 18) of the total resistance Rtotal of the channel of a transistor also called measurement area of the device 1, FIG. 8 illustrates the shift of the Dirac point of a transistor or measurement area of the device 1, as a function of the monovalent salt concentration of the electrolyte 10 on the left and as a function of the pH of the electrolyte 10 on the right, FIG. 9 illustrates the response of a transistor or measurement area of the device 1 during the adsorption of the polylysine; Vds=0.8 V, FIG. 10 illustrates the response of a transistor or measurement area of the device 1 following the adsorption of the polylysine and the attachment of the probes; Vds=60 mV, FIG. 11 illustrates the response of a transistor or measurement area of the device 1 to the DNA hybridization. A transistor to which probes have been attached on the left and a control transistor to which probes have not been attached on the right; Vds=10 mV, FIG. 12 illustrates the response of one and the same transistor or measurement area of the device 1 following the variation of the concentration of the targets; the hybridization is carried out with a concentration of targets of 20 nM on the left and the concentration is 40 nM on the right; Vds=10 mV, FIG. 13 illustrates the response of a transistor or measurement area of the device 1; the hybridization is carried out with a concentration of targets of 1 nM; Vds=50 mV, FIG. 14 illustrates the response of a transistor or measurement area of the device 1 during a low-salt hybridization (KCL 10 mM). The concentration of the targets is 20 nM; Vds=10 mV, FIG. 15 illustrates the response of two transistors of the device 1 during the sense and antisense hybridizations; the detection of ARS3 on the left and the detection of ARS5 on the right; Vds=90 mV, FIG. 18 illustrates the measurement before (reference) and after hybridization for a detection of THRCA products, and FIG. 19 illustrates the response of a transistor or measurement area of the device 1 to the DNA hybridization, in a very low concentration (10 fM).

DETAILED DESCRIPTION

Figure 1:
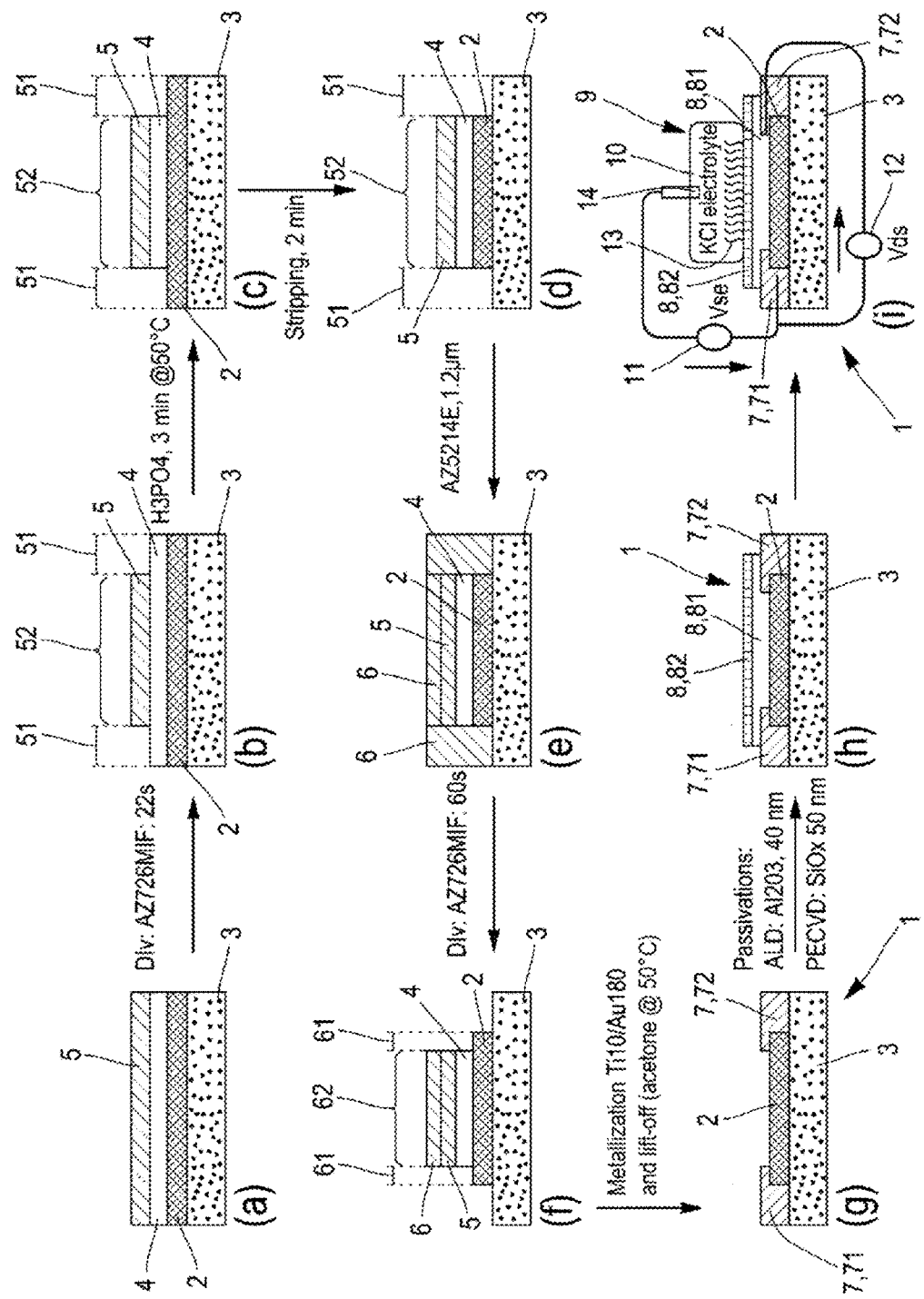
FIG. 1 is a profile sectional view of different steps of a first embodiment of a production method according to the invention (which is the preferred embodiment of a production method according to the invention) for producing a first embodiment of a device 1 according to the invention (which is the preferred embodiment of a device according to the invention)

As these embodiments are in no way limitative, variants of the invention could in particular be considered comprising only a selection of the characteristics described or illustrated hereinafter, in isolation from the other characteristics described or illustrated (even if this selection is isolated within a phrase containing these other characteristics), if this selection of characteristics is sufficient to confer a technical advantage or to differentiate the invention with respect to the state of the prior art. This selection comprises at least one, preferably functional, characteristic without structural details, and/or with only a part of the structural details if this part alone is sufficient to confer a technical advantage or to differentiate the invention with respect to the state of the prior art.

With reference to FIGS. 1 to 18, a first embodiment of a production method according to the invention, a first embodiment of a device 1 according to the invention obtained by means of this method, and a first embodiment of a method according to the invention for using the device 1 will be described first of all.

All the following production steps were carried out carefully in a cleanroom.

In the remainder of the description, the abbreviation rpm means "revolutions per minute".

Providing the Conductive Layer Under its Protective Layer

This embodiment of a method for producing a device 1 comprises providing a conductive layer 2 (with a thickness typically equal to the size of a carbon atom, which is of the order of 0.34 nm, preferably greater than 0.1 nm and/or smaller than 10 nm or even 1 nm) between a substrate 3 and a protective layer 4 (with a thickness typically greater than 0.5 nm or even 1 nm and/or smaller than 10 nm or even 5 nm).

The substrate 3 comprises or consists of silicon and/or silicon oxide, preferably silicon (preferably doped, the dopant type is preferably N/As, orientation: 100±0.5°, resistivity: 0.005 Ω·cm, thickness: 525±20 μm, diameter 100±0.3 mm) with a layer of oxidized silicon (with a thickness typically greater than 100 nm and/or smaller than 5 μm, in particular in the case where the "back gate voltage" is used) in contact with the conductive layer 2.

The protective layer 4 comprises or consists of oxidized aluminium, preferably with the formula $Al_2O_y$, where y is an integer 1.03, preferably alumina $Al_2O_3$.

At the stage of providing the conductive layer 2 between the substrate 3 and the protective layer 4, the substrate 3 is in contact with the conductive layer 2 (but not other layers, in particular not the protective layer 4).

The conductive layer 2 is in contact with the substrate 3 and the protective layer 4.

This provision step takes place as follows.

The conductive layer 2 comprises or consists of a two-dimensional conductor having a mobility (i.e. mobility of the charge carriers in the plane of the two-dimensional conductor) greater than or equal to $1,000$ $cm^2 \cdot V^{-1} s^{-1}$, preferably consisting of a layer of graphene, of silicene, of molybdenum disulfite ($MoS_2$), of germanene, of phosphorene, of stanene, or of borophene.

For illustrative but non-limitative purposes, graphene is selected for the layer 2 in the present embodiment. Throughout the remainder of the description, each of the terms conductive layer 2, two-dimensional conductor or graphene could be replaced with conductive layer 2, two-dimensional conductor, graphene, silicene, molybdenum disulfite ($MoS_2$), germanene, phosphorene, stanene, or borophene, while maintaining the validity of the description of the present invention.

CVD ("chemical vapour deposition") graphene was used for layer 2. CVD graphene is produced by catalytic dehydrogenation of methane at high temperature. The carbon atoms can then settle on a copper sheet and form a layer with a thickness of one atom depending on the conditions of growth. In order to use this graphene, it is necessary to transfer it to a substrate 3: a layer 3 of $SiO_2$ for example. Transferring the graphene 2 is an essential step during the production of the network of field-effect transistors based on graphene. In order to have a network of which all or at least the majority of the transistors work, it is necessary for the sheet of graphene 2 to be continuous; this calls for a transfer of quality.

The water from the taps in the cleanroom used contains dissolved gases ($O_2$, $CO_2$, etc.). The use thereof for rinsing during the transfer of the graphene 2 leads to the formation of aggregates of gas bubbles at the graphene-water interface. These gas bubbles burst during the drying and leave an opening in the sheet of graphene 2. In order to prevent this, the water is collected in a large beaker, which is set aside for one day before it is used. This makes it possible to degas the water, i.e. the gas bubbles rise and burst on the surface.

During the growth, graphene forms on both faces of the copper sheet, but the graphene obtained on each of the two faces of said copper sheet is not of the same quality; the graphene of the upper face has the best quality. In fact, as the lower face is placed against the oven, it is not subjected to the same heat treatments. Despite the exceptional mechanical properties of the graphene, its thickness of a few atomic layers makes it difficult, or even impossible, to transfer samples of graphene of the order of a centimetre without causing the material to break.

For this reason, the majority of the graphene transfers are carried out by adding a mechanical support in order to facilitate its manipulation. The most used material for transferring the graphene obtained by growth on copper is a layer of polymer, preferably polymethyl methacrylate (PMMA). This polymer can be applied by simple spin coating at a rotational speed ranging between 1,000 and 4,000 revolutions per minute (rpm). The thickness of the layer of the polymer can also be adjusted by using PMMA with a varied molecular mass, typically between 450,000 and 996,000 g/mol and using different concentrations of the PMMA. Optimizing these parameters makes it possible to obtain a layer of PMMA with an ideal thickness, which has sufficient mechanical strength while remaining flexible, which guarantees a good conformity between the graphene 2 and the copper substrate. After deposition, the layer of PMMA is annealed for 6 minutes at a temperature of approximately 160° C.

As mentioned above, both faces of the copper sheet are exposed to the precursors and there is therefore growth on each of them. In order to prevent the second, "lower", layer of graphene from adhering to the first, "upper", layer of graphene during the transfer, it is preferable to remove it before dissolving the metallic support. The graphene of the lower face can then be etched by RIE ("Reactive-Ion Etching") at a pressure of 10 nbar for 2 minutes. With regard to the dissolution of the copper metallic support, different chemical solutions can be used. Although it is possible to use concentrated acids such as nitric acid, their use is not recommended, because there is generally a production of hydrogen bubbles during the dissolution of the metal, which risk damaging the graphene. To dissolve nickel, it is possible to use an aqueous solution of iron (III) chloride ($FeCl_3$) in a concentration of 1 M or a solution of HCl diluted to 3%. As regards the copper, several solutions can be used, such as a solution of iron (III) nitrate ($Fe(NO_3)_3$) in a concentration of 0.05 g/ml, a commercial solution for etching copper (CE-100, from Transene) or preferably a 0.05-0.1 M solution of ammonium persulfate.

When the copper sheet is completely dissolved, the film of the PMMA-graphene assembly floating on the surface of the solution is then rinsed several times in previously degassed deionized water then recovered directly on the desired substrate 3, here Si/$SiO_2$ treated as described in the following paragraph. The samples are then dried under a hood for a few hours. In order to improve the adhesion of the graphene 2 to the substrate 3, it is advised to gently heat the sample to 160° C. The PMMA can now be dissolved in acetone at 50° C. for at least 15 minutes, then rinsed with isopropanol (IPA). The use of the blow gun is prohibited once the graphene 2 has been transferred, in order to prevent it from being damaged. Before any lithography, the graphene 2 must be protected in order to prevent direct contact thereof with the resin and the developer. For this, a layer 4 of 1 nm of aluminium oxide, deposited using the ALD ("Atomic Layer Deposition") technique is used. The deposition by means of ALD is a sequential deposition of aluminium atoms originating from the precursor trimethyl-aluminium (TMA) and oxygen atoms originating from the water. For a deposition of 1 nm, 10 cycles (at a rate of 1 A°/cycle) at a pressure of 300 mTorr and at a temperature of 175° C. are needed. What the process is for ensuring that this layer 4 effectively protects the graphene will be explained later.

The cleaning of the substrate 3 makes it possible to have a good surface quality. The elimination of the organic waste is effected by means of cleaning based on standard solvents. A first acetone bath for 5 minutes makes it possible to remove these organic particles, in particular the resins. Then in isopropanol; this last bath makes it possible to remove the acetone and to remove all traces during the drying. A last step of oxygen plasma treatment is necessary in order to make the surface of the substrate hydrophilic. This makes a good spread of the graphene sheet possible and improves the adhesion thereof to the substrate.

Once the transfer has been completed, it is now possible to move on to the lithography steps which make it possible to cut the graphene 2 and define the patterns of the electrodes, then on to the step of metallizing.

In an alternative, the assembly of the conductive layer 2 between a substrate 3 and a protective layer 4 can be bought directly assembled.

Lithographies

The lithography is the technological step needed to transfer the patterns present onto a mask. The transfer is effected on photosensitive resin spread out on the surface where it is desired to print the patterns. By exposure to sunlight, the exposed resin reacts and its structure changes. It is then possible to selectively remove either the exposed parts or the protected parts. There are several types of resin: positive resins (of which the parts exposed to ultraviolet UV rays will be removed) and negative resins (of which the exposed parts remain after developing). Other resins making both types of lithography possible are called reversible. They can behave like a positive or negative resin depending on the treatments of exposure to sunlight and of annealing to which they are subjected. The one used is AZ5214E from Sigma, the main constituent of which is the solvent methoxy propyl acetate (PGMEA), with a water content of 0.5%, a viscosity is 2451, a sensitivity spectrum is from 310 to 420 nm and an absorption coefficient at 377 nm is 0.76. The inversion process requires an additional step of annealing and flood exposure to sunlight.

Preparation Lithography of the Substrate 3

This lithography is carried out on the substrate 3 before the transfer of the layer 2 onto the substrate 3.

For this embodiment, a substrate 3 of silicon oxide is used, the silicon oxide of which forms a thickness of 1 μm on a thick layer of non-oxidized silicon. Although the optical contrast with this thickness does not make it possible to see the graphene 2 well, it does at least make it possible to prevent current leakages between the source and the gate, even for the relatively large size of the electrodes. These substrates 3 are first cut into small pieces (1.2 cm×1.2 cm) then cleaned with acetone for 5 minute(s) and rinsed with IPA. The lithography is then carried out, which makes it possible to print the alignment crosses on the substrate 3. These crosses will make it possible to be aligned on the graphene channels 2 which are completely invisible over 1

μm of SiO$_2$ underneath the resin. It is then necessary to make an opening in the resin and carry out the metallization.

This is a negative lithography comprising the following steps:
  a. annealing the substrate to evaporate the water: 5 minutes at 120° C.
  b. AZ5214E resin coating: 30 s at 4,000 rpm
  c. annealing: 2 minutes at 110° C.
  d. exposure using the corresponding mask: alignment and exposure 2 s. The exposure power is of the order of □7.5 mW/cm$^2$ with a wavelength λ=420 nm
  e. annealing: 2 minutes at 125° C.
  f. exposure without a mask: "flood exposure" for 15 s. The exposure power is of the order of □7.5 mW/cm$^2$ with a wavelength λ=420 nm
  g. developing: AZ 726 MIF, 35 s. This developer reveals the patterns printed on the resin AZ5214E, and its main constituent is "tetramethylammonium hydroxide" TMAH at 2.38%
  h. metallization: Cr 5 nm/Au 180 nm
  i. "lift-off": acetone 50° C., 15 minute(s) and rinsing with IPA The following two lithographies are carried out after the transfer of the layer 2 onto the substrate 3.

1$^{st}$ Lithography of the Transistors: Lithography of the Protective Layer 4 and of the Graphene 2

Figure 2:
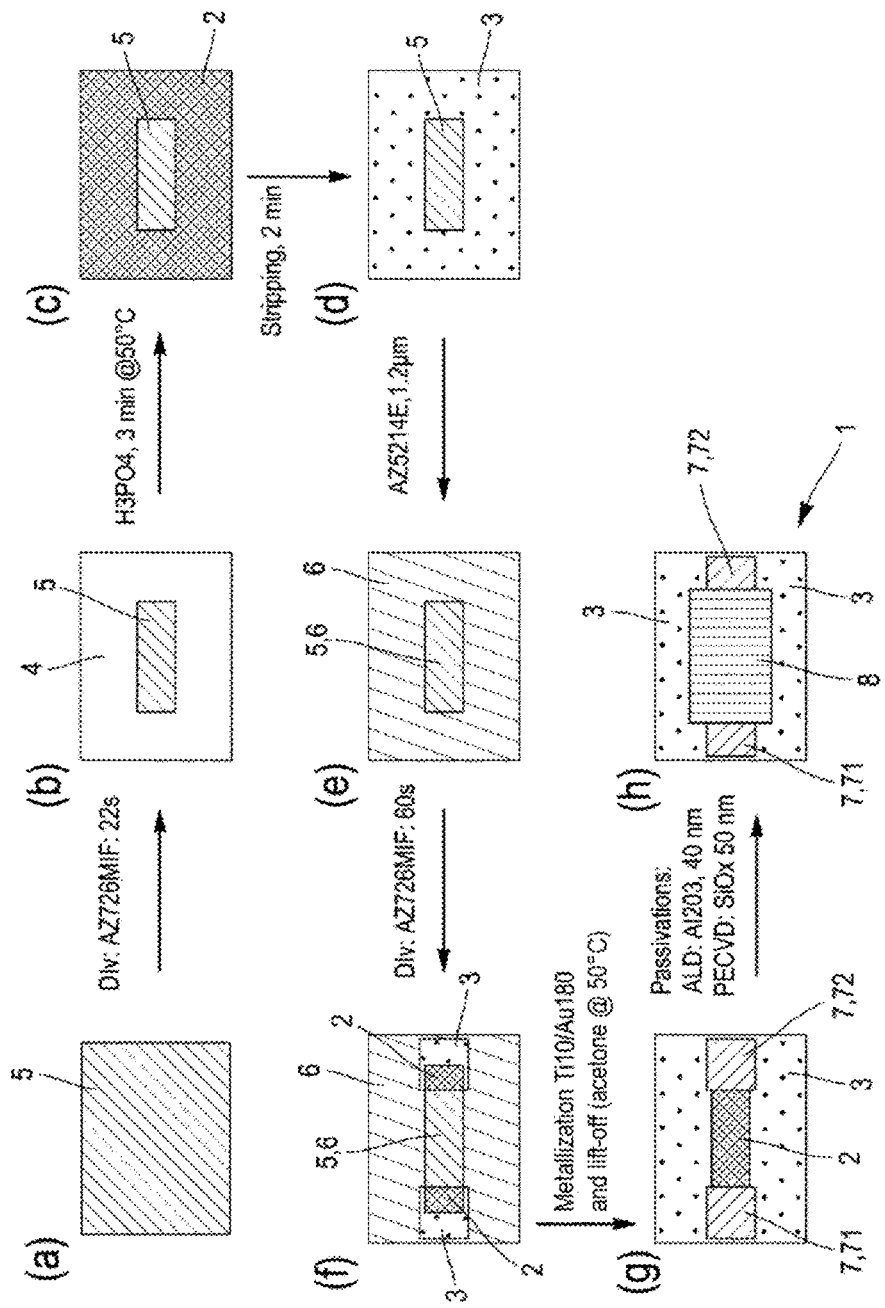
FIG. 2 is a top view of different steps of the first embodiment of a production method according to the invention for producing the device 1.

This embodiment of a method according to the invention moreover comprises:
  depositing a first lithography resin layer 5 (with a thickness typically greater than 1 μm and/or smaller than 2 μm, typically of approximately 1.2 μm) above or on the protective layer 4 such that the protective layer 4 is comprised between the conductive layer 2 and the first resin layer 5; this is illustrated in part a) of FIGS. 1 and 2. The protective layer 4 is then in contact with the first resin layer 5 and the conductive layer 2 (but not other layers); and
  a first lithography comprising:
  a) removing, in at least one removal area 51 of the first lithography, the superimposition of the first resin layer 5, the protective layer 4 and the conductive layer 2, and
  b) preserving, in at least one preservation area 52 of the first lithography, the superimposition of the first resin layer 5 (which can, however, be partially damaged or refined, but without the presence of a hole which would give access to the conductive layer 2 or to the protective layer 4), the protective layer 4 and the conductive layer 2. This is illustrated in parts b), c), and d) of FIGS. 1 and 2.

The expression "above" the layer A is used to state that there is not necessarily contact with the layer A.

The expression "on" the layer A is used to state that there is contact with the layer A, i.e. "in contact with".

Thus, the first lithography selectively removes parts of the first resin 5 and selectively preserves other parts of the first resin 5, and removes parts of the protective layer 4 superimposed on the removed parts of the first resin 5 and removes parts of the conductive layer 2 superimposed on the removed parts of the protective layer 4.

This first lithography makes it possible to draw the future areas for cutting of the graphene 2, typically into 48 pieces of 60 μm by 10 μm. It then involves printing the patterns of the corresponding mask in positive lithography on the substrate 3 onto which the graphene 2 has already been transferred and protected.

These steps are preferably carried out as follows:
  a. coating with the layer 5 of resin AZ5214E above or preferably directly on the protective layer 4 such that the protective layer 4 is comprised between the conductive layer 2 and the first resin layer 5: 30 s at 4,000 rpm; this is illustrated in part a) of FIGS. 1 and 2
  b. annealing: 2 minutes at 110° C.
  c. exposure using the corresponding mask: alignment and exposure for 15 s. The exposure power is of the order of □7.5 mW/cm$^2$ with a wavelength λ=420 nm
  d. developing: AZ 726 MIF, 22 s; this is illustrated in part b) of FIGS. 1 and 2
  e. etching the protective layer: H$_3$PO$_4$ at 50° C., 3 minutes, rinsing with water 2 minutes; this is illustrated in part c) of FIGS. 1 and 2
  f. etching the undesired graphene: stripping, 2 minutes; this is illustrated in part d) of FIGS. 1 and 2. For the etching of the monolayer graphene 2, an RIE ("Reactive-Ion Etching") plasma oxygen treatment for 2 minutes at 10 nbar is needed Contrary to what a person skilled in the art is encouraged to do, after this last step the resin 5 is not dissolved on the 48 pieces of graphene 2 protected by the layer 4 (1 nm) of Al$_2$O$_3$ (ALD) before moving on to the second, following lithography described hereinafter. In fact, the alumina 4 adheres poorly to the graphene 2 (due to its hydrophobic nature), which means that, whatever the precautions taken during this operation, the alumina 4 would risk being removed at certain locations and exposing the graphene 2 to the resin and to the other organic waste that can be found in the solvent.

2$^{nd}$ Lithography of the Transistors: Lithography of the Protective Layer 4

Thus, according to this embodiment according to the invention the substrate 3 is again resin-soaked with resin 6 for the purposes of the 2$^{nd}$ lithography (called contact lithography, for the purposes of the metallization of the graphene 2), which is a negative lithography where the resin 5 preserved on the graphene 2 is treated again with negative lithography. This embodiment of a method according to the invention thus moreover comprises:
  depositing, at least on the at least one preservation area 52 of the first lithography, preferably on the at least one removal area 51 and on the at least one preservation area 52 of the first lithography, a second lithography resin layer 6 (with a thickness typically greater than 1 μm and/or smaller than 2 μm, typically of approximately 1.2 μm) without removing the first resin layer 5 of the at least one preservation area 52 of the first lithography; this is illustrated in part e) of FIGS. 1 and 2; the first resin layer 5 is then in contact with the second resin layer 6 and the protective layer 4 (but not other layers). The second resin layer 6 is then in contact with the first resin layer 5 and the substrate 3 (but not other layers, except on the edges of the layers 2 and 4)
  a second lithography comprising: a) removing, in at least one removal area 61 of the second lithography, the superimposition of the second resin 6, the first resin 5 and the protective layer 4, but not the conductive layer 2; this is illustrated in part f) of FIGS. 1 and 2
  b) preserving, in at least one preservation area 62 of the second lithography, the superimposition of the second resin 6, the first resin 5, the protective layer 4 and the conductive layer 2; this is illustrated in part f) of FIGS. 1 and 2

It is noted that the first lithography is a positive or negative lithography and the second lithography is a negative or positive lithography respectively, the first resin layer 5 and the second resin layer 6 being constituted by one and the same resin compatible for a positive lithography and for a negative lithography.

It is noted that the resin of the first resin layer 5 and the resin of the second resin layer 6 are arranged to react, during a lithography step, to the same developer and/or to the same duration, power and wavelength of a preferably ultraviolet radiation (i.e. with a wavelength greater than 10 nm and/or smaller than 380 nm).

This embodiment of a method according to the invention moreover comprises:
- depositing, in the at least one removal area 61 of the second lithography, at least one (preferably several) electrode(s) 7 in electrical contact with the conductive layer 2, preferably in contact with part but not all of the conductive layer 2 for each measurement area.
- after the deposition of the at least one electrode 7, removing, in the at least one preservation area 62 of the second lithography, the superimposition of the second resin 6, the first resin 5 and optionally also the protective layer 4, but not the conductive layer 2.

In practice, as illustrated in FIG. 4, N (N being an integer greater than one) measurement areas are produced, i.e. N (forty-eight in the present embodiment) areas of conductive layer 2 isolated from each other.

N+1 electrodes 7 are deposited:
- one electrode 7, 72 (called drain) per measurement area in contact with the conductive layer of this measurement area but not with the conductive layer of the other measurement areas
- one electrode 7, 71 (called source) common to all the measurement areas and in contact with the conductive layer of each measurement area This is illustrated in part g) of FIGS. 1 and 2.

This second lithography makes it possible to define the patterns of the electrodes for the purposes of the next metallization. These steps are preferably carried out as follows:
a. annealing the substrate to evaporate the water: 5 minutes at 120° C.
b. AZ5214E resin coating: 30 s at 4,000 rpm
c. annealing: 2 minutes at 110° C.
d. exposure using the corresponding mask: alignment and exposure for 2 s. The exposure power is of the order of □7.5 mW/cm² with a wavelength λ=420 nm
e. annealing: 2 minutes at 125° C.
f. exposure without a mask: "flood exposure" for 15 s. The exposure power is of the order of □7.5 mW/cm² with a wavelength λ=420 nm
g. developing: AZ 726 MIF, 1 minute(s)
h. etching the protective layer on the contacts: $H_3PO_4$ at 50° C., 3 minute(s), rinsing with water 2 minutes
i. metallic deposition (Ti10/Au180) by evaporation
j. lift-off: acetone 50° C., 15 minutes and rinsing with IPA
Each electrode therefore typically comprises a first layer of titanium (with a thickness typically greater than 4 nm and/or smaller than 20 μm, typically of 10 nm) on which a second layer of gold is located (with a thickness typically greater than 50 nm and/or smaller than 250 nm, typically of 180 nm).

Passivation

This embodiment of a method according to the invention moreover comprises, after the removal (in the at least one preservation area 62 of the second lithography) of the superimposition of the second resin 6 and the first resin 5 (and the protective layer 4) but not the conductive layer 2, depositing a passivation layer 8 (with a thickness typically greater than 10 nm and/or smaller than 400 nm, typically of 90 nm) in contact with the conductive layer 2 and/or the protective layer 4 of the at least one preservation area 62 of the second lithography and in contact with at least part of each electrode 7.

This is illustrated in part h) of FIGS. 1 and 2.

The passivation layer 8 comprises an oxide and/or a nitride (for example $Si_3N_4$).

The passivation layer 8 comprises a superimposition of two different dielectric materials.

The passivation layer 8 (with a thickness typically greater than 10 nm and/or smaller than 400 nm, typically of 90 nm) preferably comprises a superimposition of two different oxides.

The passivation layer 8 comprises a superimposition:
- of a first passivation sub-layer 81 (with a thickness typically greater than 5 nm and/or smaller than 200 nm, typically of 40 nm), comprising a mixture of oxygen and aluminium atoms, preferably with the formula $Al_2O_x$, where x is an integer 1≤x≤3, preferably comprising or consisting of $Al_2O_3$, and in contact with the conductive layer 2. This layer 81 is deposited by ALD (400 cycles, T=175° C., P=300 mTorr); then
- of a second passivation sub-layer 82 (with a thickness typically greater than 5 nm and/or smaller than 200 nm, typically of 50 nm), comprising a mixture of oxygen and silicon atoms, preferably comprising or consisting of silicon oxide preferably with the formula $SiO_z$, where z is an integer 1≤z≤2, and in contact with the first sub-layer of the passivation layer, such that the first sub-layer 81 of the passivation layer is comprised between the conductive layer 2 and the second sub-layer 82; this layer 82 is deposited by PECVD (T=280° C., heating: 1 min, —Stabilization: 10 s, -, —Surface preparation: 10 s, —Time for deposition: 5 s, —$SiH_4$ supply: 5 s, —Deposition: 1 min 53 s)

The passivation layer 8 has a breakdown field greater than or equal to $10^6$ V·m$^{-1}$.

It is in fact preferable to protect the obtained embodiment of a device 1 according to the invention against the impurities and water molecules in the ambient air and to stabilize its electrical characteristics.

The choice of the nature and thickness of the oxide of the passivation layer 8 depends on its resistance to the measurement electrolyte 10 during the electronic detection and its impermeability. Two types of oxide have been combined: aluminium oxide $Al_2O_3$ deposited by ALD and silicon oxide deposited by PECVD.

In fact, the quality of the alumina deposited by ALD is very good but it does not stabilize the electrical characteristics of the transistors and in addition is quickly destroyed by the electrolyte 10 during the electronic detection. It is used only for its impermeability properties. The combination of it with silicon oxide makes it possible to stabilize the devices and to take detection measurements, being limited to [−1V,1V] for the source electrolyte voltage; the electrochemical phenomena appear when this voltage range is exceeded.

Figure 3:
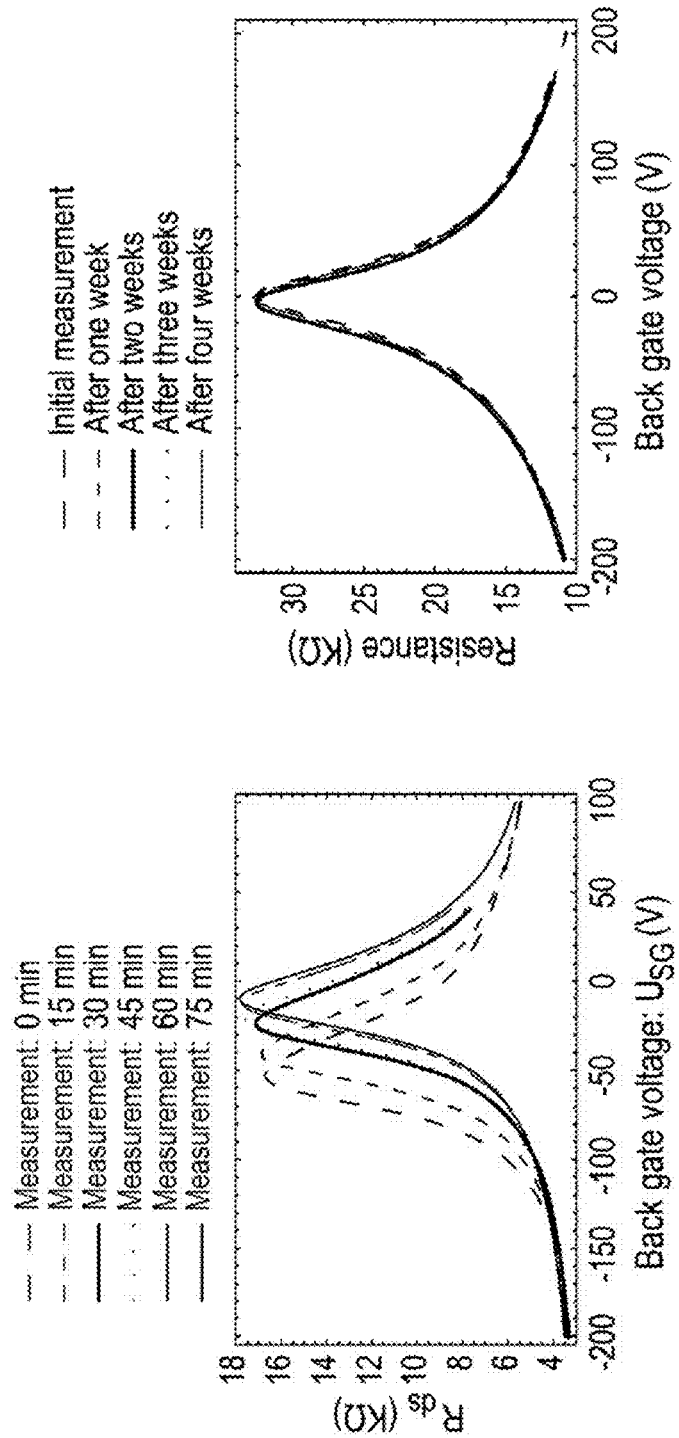
FIG. 3 illustrates the time drift of the resistance of a measurement area of the conductive layer with dimensions, in the plane of FIG. 2, of 10 μm by 25 μm (on the vertical axis) with respect to the voltage applied between the back gate and the source ("back gate voltage"; in this configuration measurements of from −200 V to 200 V are taken) (on the horizontal axis) of the device 1, for a passivation layer 8 comprising only 40 nm of $Al_2O_3$ (deposition by DLA) on its left-hand part and for a passivation layer 8 comprising 40 nm of $Al_2O_3$ (deposition by DLA) then 50 nm of $SiO_2$ (deposition by PECVD, "Plasma-Enhanced Chemical Vapour Deposition") for its right-hand part.

FIG. 3 illustrates the technical advantage of such a passivation layer 8 comprising a superimposition of two different oxides:
- the left-hand part of FIG. 3 illustrates, for a passivation layer 8 comprising only 40 nm of $Al_2O_3$ (deposition by ALD), the time drift of the resistance of a channel (on the vertical axis) with respect to the gate-source voltage (on the horizontal axis) obtained under the following experiment conditions: ambient temperature, without electrolyte 10.

the right-hand part of FIG. 3 illustrates, for a passivation layer 8 comprising 40 nm of $Al_2O_3$ (deposition by ALD) then 50 nm of $SiO_2$ (deposition by PECVD), the time drift of the resistance of a channel (on the vertical axis) with respect to the gate-source voltage (on the horizontal axis) obtained under the following experiment conditions: ambient temperature, without electrolyte 10.

In FIG. 3, a much smaller time drift is observed on the right than on the left-hand part in FIG. 3.

It is noted that FIGS. 1 and 2 are only partial views of the different layers 2, 3, 4, 5, 6, 7 and 8 for a single measurement area.

In practice, as illustrated in FIG. 4 (for which the passivation layer 8 has already been deposited on the graphene 2), at least one measurement area is produced, preferably several measurement areas, i.e. several (forty-eight in the present embodiment) areas of conductive layer 2 protected by a passivation layer 8 corresponding to the different (forty-eight) drains 7, 72.

This embodiment of a production method according to the invention can moreover comprise depositing a layer 13 of polymer and/or of nucleotides in contact with the conductive layer 2 or in contact with the passivation layer 8. The nature and the use of this layer 13 is detailed hereinafter.

Device 1 According to the Invention

The embodiment of a device 1 according to the invention obtained by means of the embodiment of a production method according to the invention described previously therefore comprises:

the substrate 3,
the conductive layer 2 divided into the at least one measurement area, typically at least 10 measurement areas, typically 48 measurement areas, in FIG. 4,
the at least two distinct electrodes 7, 71, 72 in contact with the conductive layer 2.

The conductive layer 2 preferably consists of a two-dimensional conductive layer (preferably of graphene) having (preferably for each measurement area):

a doping level lower than $10^{11}$ impurities (preferably charged impurities) per $cm^2$, and/or
a shift of the voltage of the Dirac point with respect to 0 volts of less than 1 volt in absolute terms, the voltage of the Dirac point being measured on a variation curve of the resistance of the conductive layer 2 of a single measurement area considered as a function of the "back gate voltage" (i.e. the voltage between the layer 3 and the electrode 71) in the absence of electrolyte 10, the Dirac point being the point on this curve having the voltage closest to zero with a zero second derivative and/or a maximum resistance value.

The doping of the graphene 2 can in fact be controlled by applying an external field. By changing the sign of the potential difference, it is possible to pass continuously from a doping with electrons to a doping with holes. Thus, for a positive back gate voltage the mobility is ensured by the electrons, and the holes take on the conductivity for a negative back gate voltage. The neutrality point between the conductivity in holes and in electrons (charge neutrality point) is called the Dirac point.

Each "impurity" considered is:

each presence of an atom outside the crystallographic lattice of the two-dimensional conductor 2 (here graphene), or
each absence of an atom in the crystallographic lattice of the two-dimensional conductor 2 (here graphene).

An impurity is charged if it is electrically charged, negatively or positively.

The device 1 moreover preferably comprises the passivation layer 8 having a breakdown field greater than or equal to $10^6$ $V \cdot m^{-1}$ and covering the conductive layer 2 and at least part of each electrode 7, such that the conductive layer 2 and at least part of each electrode 7 are located between the substrate 3 and the passivation layer 8. In some variants, however, this layer 8 can be absent.

The conductive layer 2 comprises at least one measurement area, and is preferably divided into several measurement areas which are distinct and separated from one another.

Each measurement area consists of an area of conductive layer 2 inserted between the substrate 3 and the passivation layer 8.

The electrodes 7 comprising:
the common source 7, 71 in contact with all the measurement areas and
one drain 7, 72 per measurement area, each drain 72 being in contact with only a single measurement area.

The device 1 comprises an electrode 14. This electrode is typically an Ag/AgCl electrode.

The device 1 moreover comprises a tank 9 arranged to receive an electrolyte 10 (such that the electrode 14 is immersed in this electrolyte 10) above the conductive layer 2, preferably such that the electrolyte 10 is in contact with the passivation layer 8, or with the conductive layer 2 if this passivation layer 8 is absent.

The device 1 comprises means 11 for measuring and/or imposing:

a voltage Use, also called Vse, and/or an electric intensity Ise between the electrolyte 10 (or the electrode 14) and the source electrode 71, and/or
a voltage $U_{SG}$, also called $V_{SG}$, and/or an electric intensity $I_{SG}$ between the gate (i.e. the substrate 3, more precisely the doped and non-oxidized layer of the substrate 3 separated from the layer 2 by the oxidized and undoped layer of the substrate 3) and the source electrode 71
a voltage $U_{SG}$, also called $V_{SG}$, and/or an electric intensity $I_{SG}$ between another possible gate and the source electrode 71. This other gate can be a gate electrode produced on the measurement area or on each measurement area of the conductive layer 2, such that the layer 2 is located between the substrate 3 and this other gate. This other gate can be present (in the absence or in the presence of the layer 8 and/or in the absence or in the presence of the layer 4) in a variant of the invention for which the production method according to the invention comprises producing a gate electrode realized on the measurement area or on each measurement area of the conductive layer 2, such that the layer 2 is located between the substrate 3 and this other gate (with or without the production or presence of the layer 8 and/or with or without the production or presence of the layer 4).

The device 1 comprises means 12 for measuring and/or imposing a voltage Uds, also called Vds, and/or an electric intensity Ids between the source electrode 71 and one of the drain electrodes 72, preferably in turn for each drain electrode 72.

These means 11 and 12 typically comprise electronic and/or computing means, such as for example those described in the article "Spatially resolved electronic detection of biopolymers", Pouthas et al., PHYSICAL REVIEW E70, 031906(2004) (in particular in FIG. 2 thereof).

Both modes, imposed current and imposed voltage, are possible.

Typically, Vds is imposed and Ids is measured, and the following is also imposed:

$V_{SG}$ in a gate configuration, the gate being the substrate 3 or more conventionally the other gate electrode as described previously Vse in another configuration.

The device 1 comprises a layer 13 of polymer and/or of nucleotides above the at least one measurement area, in contact with the conductive layer 2, in contact with the protective layer 4 if this layer is present, or in contact with the passivation layer 8 if this passivation layer is present.

The substrate 3 is in contact with the conductive layer 2 and the electrodes 7, 71, 72 (but not other layers, in particular not the passivation layer 8).

The conductive layer 2 is in contact with the substrate 3 and the passivation layer 8 (and at least two electrodes 7, preferably the source 71 and one of the drains 72).

The device 1 has been characterized, in particular for each transistor or measurement area, its Dirac point and its mobility, as detailed below.

Dirac Point

The graphene 2 is transferred onto a substrate 3 of $P^{++}Si/SiO_2$ (positively doped silicon covered with a layer of silicon oxide) which makes it possible to produce an electric field effect. Actually under the sheet of graphene 2 there is 1 μm of silicon oxide, which is an insulator, before the non-oxidized silicon itself is reached. This is very highly doped (chemically) in order to make it metallic. If a potential difference is applied between the doped silicon (the back gate) and the graphene sheet (the source), a capacitor is produced (and, in the presence of the source contacts and drain, a field-effect transistor), the dielectric of which is silicon dioxide. By means of the electric field effect, regulating the potential difference, it is possible to add or remove the electrons to or from the graphene 2. As the non-doped graphene 2 does not contain charge carriers, an external "button" is then available for electrically controlling the doping with charge carriers. By changing the sign of the potential difference, it is possible to pass continuously from a doping with electrons to a doping with holes. Thus, for a positive back gate voltage the mobility is ensured by the electrons, and the holes take on the conductivity for a negative back gate voltage.

FIG. 5 illustrates the "back gate voltage" (i.e. between the layer 3 and the electrode 71) dependence on the resistance of a monolayer graphene sheet 2 (i.e. a single measurement area):

on curve 15 for the device 1 according to invention on curve 16 for a device for which the resin layer 5 is completely dissolved at the end of the first lithography of the protective layer 4 and the graphene 2 before the deposition of the resin 6.

In this case a voltage $U_{ds}$ of 0.5 V was imposed. The layer 8 is indeed present. FIG. 6 illustrates:

on the left, the "back gate voltage" (i.e. between the layer 3 and the electrode 71) dependence on the resistance of a monolayer graphene sheet 2 (i.e. a single measurement area) for another device for which the resin layer 5 is completely dissolved at the end of the first lithography of the protective layer 4 and the graphene 2 before the deposition of the resin 6, on the right, the voltage of the Dirac point as a function of the number (1 to 48) of the measurement area (i.e. index of the measurement area, also called index of the transistor) for this other device, before annealing on curves 29 and 30 and after annealing on curves 36 and 37. For such an annealing, this other device is introduced into the body of an oven for one day in order to generate a vacuum of around $5\cdot10^{-6}$ mbar. The supply voltage of an LED is then increased, which makes it possible to heat, by Joule effect, the enclosure where this other device is placed. The temperature can then be increased to 280° C. for a supply voltage of 36 V. The annealing starts once the desired temperature has been reached. On the network shown, an annealing of 48 hours at 280° C. was carried out. After the annealing, a clear decrease in the doping level and an improvement of the mobility of the transistors is observed.

The very low value of the Dirac point for the device 1 according to the invention is observed, much closer to zero than curve 16 in FIG. 5 (without annealing) or than curve 36 in FIG. 6 (with annealing).

The invention makes a lower voltage value of the Dirac point (or "charge neutrality point" ($V_{CNP}$)) possible, and makes it possible to prevent an annealing which has the drawback of generally increasing the contact resistance of the electrodes 7.

On curve 15 in FIG. 5, the value of the voltage at the Dirac point is 0 volts.

Mobility

The invention prevents a reduction of the mobility because it protects the graphene 2 from an introduction of defects or impurities (charged or not charged).

The mobility of the transistors of the device 1 is estimated by minimizing the mean squared deviation between the experimental data (curve 17 in FIG. 7) and the theoretical formula (curve 18 in FIG. 7) which describes the total resistance $R_{total}$ of the channel. The mobility of the charge carriers for this transistor is estimated at 3,732.5 cm² V⁻¹ s⁻¹.

The formula used is indicated on the right in FIG. 7, where:

$V_g$ is the back gate voltage.

$V_{dp}=0$ V: Voltage at the Dirac point.

$C_g=34.5\cdot10^{-10}$ F·cm⁻²: Capacity of the gate oxide $n_0=5.11\cdot10^{11}$ cm⁻²: Charge density of the impurities.

L=25 μm: Length of the channel

W=10 μm: Width of the channel

μ=1,301.42 cm²/Vs: Mobility of the charge carriers e is the elementary charge of a proton (e=1.602·10¹⁹ C)

$n=C_g(U_g-U_{dg})/e$: charge density induced by the gate.

For $U_g$=i.e., $n_0=-C_g U_{dp}/e$, for the intrinsic graphene, $n_0=0$ i.e., $U_{dp}=0$.

Si $U_g \leq U_{dp}$, conduction through the holes.

Si $U_g \geq U_{dp}$, conduction through the electrons.

$R_{contact}=9,000$ Ω

Method According to the Invention for Using the Device 1.

The first embodiment of the method according to the invention for using the device 1 comprises a step of detecting the attachment of atoms or molecules (or even of biological cells) above or directly on (i.e. in contact with):

the conductive layer 2 of each measurement area if the passivation layer 8 is absent, or the protective layer 4 if this layer is present, or the passivation layer 8 if the passivation layer 8 is present.

The attachment is preferably an attachment of atoms or molecules (or even of biological cells) on a layer of polymer and/or of nucleotides attached to the conductive layer 2 or to the passivation layer 8 beforehand.

The attachment is preferably a hybridization of nucleotides on a layer 13 of polymer (typically of polylysine) and of nucleotides (preferably of oligonucleotides comprising 10 to 50 bases, typically 20 bases) located above the at least one measurement area, and in contact with the conductive layer 2 or in contact with the passivation layer 8.

For this detection step, the electrode 14 is immersed in the electrolyte 10. In the configuration where the charge carriers created by field effect are provided by the doped silicon 3 performing the function of a metallic gate, the back gate voltage was modulated over the interval [−200V,200V]. The doping of the graphene 2 is then controlled by the holes and the electrons coming from the silicon 3. In this situation, the physicochemical properties are quite stable and do not affect the behaviour of the graphene 2 from one measurement to another if the stabilization has been done well. The situation can also be reversed, by using the passivation layer (40 nm $Al_2O_3$ deposited by ALD and 50 nm $SiO_2$ deposited by PECVD) as dielectric and an electrolyte 10 performing the function of the gate which provides the ions for controlling the doping of the graphene. In this case, the properties of the electrolyte 10 can be easily modified and as a result it can be seen how the graphene 2 behaves. The nature of the ions of the electrolyte 10, its concentration, its pH and even the charge density at the interface of the electrolyte 10 and the passivation layer 8 are changed by locally depositing the charged molecules as a solution of DNA (input of negative charge) or a solution of (positively charged) poly-L-lysine. It was possible to observe the shift of the Dirac point by changing certain properties of the electrolyte 10.

The electrolyte 10 used is preferably a solution of KCl or NaCl.

The electrolyte 10 (typically KCl or NaCl) typically has a concentration higher than 10 μM, preferably higher than 10 mM, preferably higher than 20 mM and/or lower than 80 mM, preferably lower than 50 mM.

This makes it possible to keep the Dirac point as close to 0 volts as possible.

The electrolyte 10 used preferably has a pH higher than 6 and/or lower than 8. For example, the pH of a solution of KCl is adjusted with KOH.

This makes it possible to keep the Dirac point as close to 0 volts as possible.

In FIG. 8:
- FIG. 8a) illustrates, for the device 1, the variation in the voltage at the Dirac point $V_{DP}$ for a measurement area as a function of the concentration of the electrolyte 10 of KCl. Solutions of KCl with different concentrations are prepared; the electrode 14 and the tank 9 are rinsed with deionized water then dried in compressed air after each measurement point and
- FIG. 8b) illustrates, for the device 1, the variation in the voltage at the Dirac point $V_{DP}$ for a measurement area as a function of the pH of the electrolyte 10 of 25 mM of KCl, the pH of which is adjusted by a basic solution of KOH.

FIGS. 9, 10, 11a), 11b), 12a), 12b), 13, 14, 15a), 15b), 16a), 17b) and 18 illustrate a measurement of electric current Ids flowing between the source 71 and a drain 72 (connected by a measurement area, each measurement area corresponding to a "transistor") of the device 1 according to the invention as a function of an imposed electric voltage $U_{SE}$ between the source 7, 71 and the electrode 14 immersed in the electrolyte.

With reference to FIG. 9, polylysine is a polymer widely used in the technique for attaching DNA molecules to biochips. It is positively charged and adheres easily to negatively charged surfaces like silicon oxide. The polymer layer 13 is deposited and its effect is verified as follows. A reference measurement (curve 19) is taken on the well cleaned device 1 and it is incubated in a solution of polylysine with a concentration Co/2 (where Co=85 μM) for 30 minutes, then it is left to dry for one day at ambient temperature before a detection measurement (curve 20) is performed. The device 1 is again incubated in a solution of polylysine with a concentration Co, then left to dry again for a second detection measurement (curve 21).

A positive shift of the Dirac point proportional to the concentration of the polylysine solution is observed. An input of positive charge produces a positive shift of the Dirac point. This response is proportional to the concentration of the polylysine. The sensitivity of the device 1 is typically 5 mV/μM to 30±5 mV/μM.

The different sequences used in the present description are detailed in the table below.

TABLE 1

| Name | Sequence | Functionalization | Number of bases | Complementary to |
|------|----------|-------------------|-----------------|------------------|
| Ars3 | [5']CCGCGAACTGAC TCTCCGCC[3'] | no | 20 | Ars3sens |
| Ars3sens | [5']GGC GGA GAG TCA GTT CGC GG[3'] | Cy3 or Cy5 | 20 | Ars3 |
| Ars5 | [5']CAG GCG GCA GGG CTG ACG TT[3'] | no | 20 | Ars5sens |
| Ars5sens | [5']AAC GTC AGC CCT GCC GCC TG[3'] | Cy3 or Cy5 | 20 | Ars5 |
| Ars7 | [5']TAT AGC GTA CGA ACT CCA GC[3'] | no | 20 | Ars7sens |
| Ars7sens | [5']GCT GGA GTT CGT ACG CTA TA[3'] | Cy3 or Cy5 | 20 | Ars7 |
| Lprime | [5']GGG TTT TGC TAT CAC GTT GTG[3'] | no | 21 | — |

With reference to FIG. 10, after the adsorption of the polylysine, probe oligonucleotides (1 μM) are immobilized on the device 1 (in the tank 9) by locally depositing a drop of the order of 0.1 μL. After 45 minutes of drying a detection measurement is taken, using the detection measurement of the polylysine as reference. The attachment of the probes, which is synonymous with an input of negative charge, induces a negative shift of the Dirac point. An input of negative charge produces a negative shift. For this transistor it can be seen that the whole of the polylysine was attached by the probes, which explains the shifts that are observed being opposing but of the same order of magnitude. For all of the measurement areas (each measurement area corresponding to a "transistor") of the device 1, the adsorption of the polylysine induced a shift of 1.003±0.2 V. The attachment of the probes induced a shift of −0.9±0.3 V. This seems to be logical since it is possible not to attach the whole of the polylysine and explains the importance of the different blockages (chemical and physical) produced in order to prevent the non-specific adsorptions of the targets during the hybridization. Curve 22 is a reference curve before deposition of polylysine, curve 23 is a measurement curve after deposition of polylysine but before deposition of the probe and curve 24 is a measurement curve after deposition of the probe.

With reference to FIG. 11, after the attachment of the probes, the neutralization of the residues of polylysine on the transistors examined is carried out by:

Chemical blockage: this is a step which consists of incubating the device 1 for 30 minute(s) in a solution of acetic anhydride.

Physical blockage: the device 1 (also called "chip"), after the chemical blockage, is then incubated for 30 minutes in a solution containing oligonucleotides with a different sequence from that of the complementary targets of the probes attached beforehand.

A reference measurement (curves 25 and 26) is then taken before moving on to the hybridization by incubating the device 1 in a solution containing the complementary targets of the probes.

After hybridization, a detection measurement (curves 27 and 28) is taken. FIG. 11 illustrates the response of two different measurement areas after hybridization. On the left (11*a*)), a measurement area to which the probes were attached, a shift of −20 mV is observed. On the right (11*b*)) a control measurement area to which the probes were not attached. The concentration of target is 10 nM and Vds=10 mV.

The order of magnitude of the shift on the device 1 in FIG. 11*a*) with respect to the concentration of target and the insensitivity of the control transistor in FIG. 11*b*) allows the conclusion that the shift that is observed is really due to the hybridization between the probes and the targets.

With reference to FIG. 12, the hybridization experiment was performed under the same conditions as previously, varying the concentration of the targets. During the first experiment, the concentration of the targets is 20 nM and, during the second experiment, the concentration was doubled. FIG. 12 illustrates the response of one and the same transistor following the variation of the concentration of the targets. On the left (12*a*)) the hybridization is carried out with a concentration of 20 nM and on the right (12*b*)) the concentration is 40 nM; the other experimental conditions being kept fixed (chemical blockage 30 minutes, physical blockage 30 minutes, measurement electrolyte KCl (25 mM), hybridization duration 30 minutes); Vds=10 mV. With this experiment it was noted that the transistors are sensitive to the variation of the concentration of the targets. The shifts observed on the devices 1 examined are proportional to the concentration of the targets.

With reference to FIG. 13, it is sought to know what the lowest concentration of the targets that can be detected can be. The hybridization experiment is then performed from this point of view, this time using a very low concentration of the targets (1 nM), keeping the other experimental conditions unchanged. In this case Vds=50 mV. On the basis of the results of this experiment it can be concluded that the sensitivity of the device 1 is of the order of −20 mV/nM.

The concentration of the measurement electrolyte in the preceding experiments is generally 25 mM. With reference to FIG. 14, it was then attempted to carry out the hybridization at a much lower concentration. The hybridization experiment is then performed again, using a KCl electrolyte at 10 mM. FIG. 14 illustrates the response of a transistor during a low-salt hybridization (KCl 10 mM). The concentration of the targets is 20 nM. The other experimental conditions remained unchanged. Vds=10 mV. Larger shifts were observed during this experiment on all the transistors examined. The salt concentration affects the intensity of the signal detected. The more the electrolyte is loaded with salt, the more the screening phenomena are observed and decrease the electrical signal.

During the preceding experiments, probes of the same nature, either ARS3 or ARS5, were immobilized. In the new experiment illustrated in FIG. 15, three drops of three different species were deposited in the tank 9 on the network of transistors: ARS3, ARS5 and ARS7 with a concentration of 1 μM. After the chemical and physical blockage series, two hybridization reactions were carried out. The first with the targets ARS5sensCy5 complementary to ARS5 and the second with the ARS3sensCy3 complementary to ARS3. The part of the network covered by ARS7 having remained control. It was noted that some transistors covered with ARS3 and ARS5 remained insensitive during the two hybridization series in addition to those of ARS7 (which is normal for these latter). Furthermore, transistors reacted selectively during hybridizations, as can be seen in the following figures. It can also be seen that the shifts are less pronounced during the second hybridization. FIG. 15 illustrates the response of two transistors during sense and anti-sense hybridizations:

the detection of ARS3 on the left (15*a*)) and the detection of ARS5 on the right (15*b*)). The small shift that is observed during the hybridization of ARS3 on the device 1 on the right would be due to the non-specific hybridization between ARS3sensCy3 and ARS5. Vds=90 mV. This experiment proves that the shifts that are observed during the hybridization are not random. Transistors react selectively vis-à-vis the complementary targets.

Figure 16A:
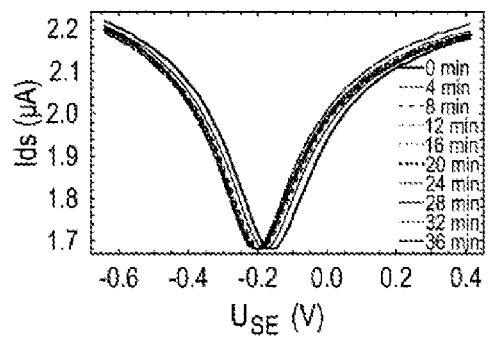
FIG. 16 illustrates the behaviour of a transistor of the device 1 in real time during the hybridization; the progression of the characteristic with complementary targets on the left and the shifts of the Dirac point with complementary targets and without targets on the right; Vds=50 mV.
Figure 16B:
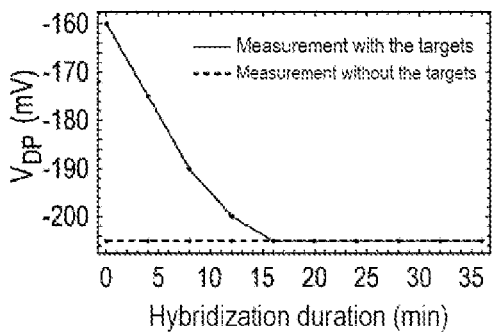
Figure 17A:
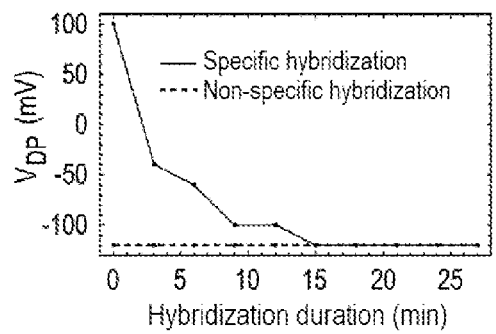
FIG. 17 illustrates the response of a transistor or measurement area of the device 1 in real time during the hybridization; the progression of the characteristic with complementary targets on the right and the shifts of the Dirac point with complementary targets and with non-complementary targets on the left; Vds=50 mV
Figure 17B:
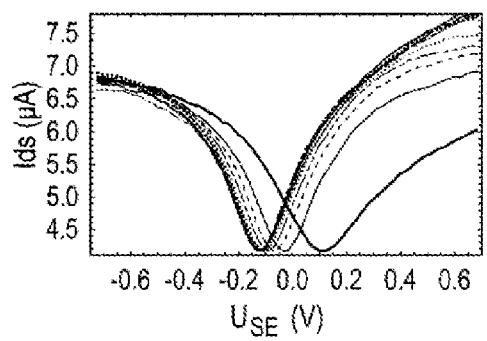

In order to see how the transistors behave in real time of the hybridization, a series of 10 measurements at time intervals of 4 minutes was launched. The hybridization buffer is 0.1×PBS. At the end of the experiment, a control test is performed with the same buffer without the targets. Drifts were observed over the first 16 minutes. These drifts are quite marked at the start, decreasing over time and finishing by dimming. Furthermore, these drifts never appeared during measurements without the targets or in the presence of the non-complementary targets. FIG. 16 illustrates the behaviour of a transistor in real time during the hybridization. On the left (16*a*)) the progression of the characteristic between t=0 minute and t=36 minutes from right to left, and on the right (16*b*)) the shifts of the Dirac point with the targets and without the targets; Vds=50 mV. FIG. 17 illustrates the behaviour of a transistor in real time during the hybridization. On the right (17*b*)) the progression of the characteristic between t=0 minute and t=36 minutes from right to left, and on the left (17*a*)) the shifts of the Dirac point with the complementary targets and with the non-complementary targets; Vds=50 mV. With this experiment, it was possible to observe the progression of the Dirac point in real time during the hybridization. The duration of the hybridization is estimated at 16 minutes, given that no shift is observed beyond this period. The speed of displacement of the Dirac point can then be calculated by calculating the slope of the specific hybridization curve in FIG. 16*b*) or 17*a*). This speed is −2.8 mV/minute. Another experiment during which the non-complementary targets were used after the specific hybridization gave the same result. The displacement of the Dirac point is estimated at −14.7 mV/min. This second experiment confirms that the detected signal is not due to the non-specific adsorption of the targets. It is indeed a reaction between the probes and their complements.

Finally, the THRCA products (for "Tagged Hyperbranched Rolling Circle Amplification") such as those described in WO2011/018774 are complex molecules constituted by a single strand part the sequence of which can be that of ARS3 or ARS5 and a double strand part which can be reproduced periodically. These are molecules which bring a lot of charge to the device 1. The hybridization of these molecules is a little more complicated than that of the oligonucleotides. As the double strand part is longer, these molecules migrate more slowly in solution than the oligonucleotides, which requires a longer hybridization time. According to the results obtained in fluorescence detection, a longer chemical blockage time is needed for a specific hybridization of the THRCA products than for a specific hybridization of the oligonucleotides. Another parameter that could be controlled during the fluorescence detection was the temperature. The hybridization at a temperature of 50° C. had considerably reduced the non-specific hybridizations. ARS3 probes with a concentration of 2 µM were attached by the polylysine, as in a normal process of hybridization of the oligonucleotides. The device 1 is then dried for 45 minutes, incubated in acetic anhydride for three hours and rinsed properly with deionized water. This blockage remains necessary even if the signal-to-noise ratio is not being analyzed. In fact, the inventors noted that not all of the polylysine is attached by the probes and, in addition, it is necessary to block the surrounding polylysine in order to prevent the preferential reaction, i.e. the attraction of the positive charges of the polylysine and the negative charges of the THRCA molecules. A solution of the targets (THRCA) is then prepared (12 µL of product in 1 mL of final PBS) and hybridized for one hour. FIG. 18 illustrates the measurement before (reference) and after hybridization. The THRCA products are long and therefore highly charged molecules. This explains the high intensity of the signal given by the transistors after the hybridization.

The experiment presented in FIG. 19 aims to determine a very low target concentration that can be detected according to the invention. Since the sensitivity of the transistors decreases during a repeated use, the experiment was performed with a freshly prepared network of field-effect transistors based on graphene (also called GFET) belonging to a device 1 according to the invention as illustrated previously, in order to have a high sensitivity.

The blocking steps prevent a non-specific adsorption and stop a large quantity of target with a low concentration from being lost in this measurement.

The concentration of the targets was fixed at 10 fM. After incubation of the chip 1 with targets for 30 min, the chip 1 was rinsed, then three detection measurements were performed every two minutes. The amplitude of the signal observed (−50 mV, shift downwards from −120 mV to −170 mV) strongly exceeded the experimental drift (the drift is not detected on the timescale, as illustrated by three data points before and three data points after the hybridization). This suggests the possibility of obtaining a detection below the femtomolar range.

A GFET next to the device 1 was measured in parallel and also detected a specific hybridization, although with a shift with a smaller amplitude (−21 mV).

The experiment was repeated with another freshly prepared GFET network according to the invention. In this case, four transistors were recorded and all of them detected the hybridization at a target concentration of 10 fM (−19, −18, −25, −22 mV).

Using another freshly prepared GFET 1, it was then attempted to detect the hybridization at a target concentration reduced by ten times (1 fM). Five transistors of the network were measured and a very small hybridization signal was observed for two of them (shifts of approximately −5 and −6 mV), but otherwise a shift which clearly exceeded the measurement uncertainty of approximately 2 mV was not observed. For the measurements presented here, the measurement uncertainty is mainly given by the accuracy of the determination of the voltage of the Dirac point, which depends on the size of the step of the discrete voltage recordings $U_{SE}$ (here 10 mV), and the width of the minimum $I_{DS}$ (which depends on the mobility of the charge carriers).

Thus, a reproducible detection of the hybridization was obtained with DNA oligonucleotides with 20 bases in a concentration of 10 fM. The hybridization of a single target molecule corresponds to the formation of 20 pairs of DNA bases. The detection limit of 10 fM of target molecules thus corresponds to a detection limit of 200 fM in terms of individual pairs of DNA bases. The high sensitivity is attributed to the good transduction capacity of the GFET networks according to the invention made possible by two original elements.

Firstly, the shifts of the Dirac point due to the incorporation of impurities during the production of a device according to the state of the art harm the sensitivity. This shift has been reduced owing to the invention by means of an innovative production process which protects the graphene during the photolithographic structuring. The GFETs as produced according to the invention have a high mobility and the positioning of the Dirac point is well defined, as shown by the current-voltage characteristics in the shape of a steep V. In fact, small threshold voltage shifts induced by the DNA hybridization are more easily resolved if the Dirac point manifests itself as an acute peak.

Secondly, a thin protective layer was used, which separates the graphene from the electrolyte solution during the DNA hybridization and the electronic measurement. This dielectric layer makes it possible to achieve both the sensitivity and the stability of the threshold voltage under the electrolyte (i.e. a very small residual drift). A good solution has been found for implementing this layer: a double layer deposited by ALD and PECVD.

The device 1 according to the invention has channels made of graphene covered with a thin insulating layer. According to the invention this layer gives a stability over time to the characteristics of the device 1 and prevents the chemical contamination of the graphene during the contact with the electrolyte solutions.

The surface in contact with the electrolyte is $SiO_2$, as for the silicon networks used according to the state of the art. In addition, the salt compositions of the electrolyte solutions used here are similar to the solutions used according to the state of the art. As anticipated, the signs of the threshold voltage changes observed according to the invention (during the adsorption of PLL, the adsorption of DNA and the DNA hybridization) coincide with those described for the silicon devices according to the state of the art.

Remarkably, the GFET devices 1 according to the invention have very small threshold voltage drifts (less than 1 mV per hour, see FIG. 19), much smaller than those observed with the devices with silicon according to the state of the art (approximately 0.2-1 mV/min, see for example J. Fritz, C. Emily, G. Suzanne, S. Peter and M. Scott, "Electronic detection of DNA by its intrinsic molecular charge," PNAS, vol. 99, no. 22, pp. 14142-14146, 2002.; K. Malpartida-Cardenas, N. Miscourides and J. Rodriguez-Manzano, "Quantitative and rapid Plasmodium falciparum malaria diagnosis and artemisinin-resistance detection using a CMOS Lab-on-Chip platform," Biosens. Bioelectron, vol. 11, no. 145, pp. 0956-5663, 2019; C. Perréard, A. Blin and U. Bockelmann, "Threshold voltage drift of FET sensor arrays with different gate insulators," Sens. Actuator B-Chem, no. 185, pp. 282-286, 2013.).

In addition, the amplitudes of the electronic signals of DNA hybridization are approximately 100 mV for the GFET networks according to the invention, greatly exceeding the typical amplitudes of from 3 to 10 mV of the FET networks with silicon according to the state of the art (see A. Blin, I. Cissé and U. Bockelmann, "Electronic hybridization detection in microarray format and DNA genotyping," Sci. Rep, vol. 4, p. 4194, 2014.; J. Fritz, C. Emily, G. Suzanne, S. Peter and M. Scott, "Electronic detection of DNA by its intrinsic molecular charge," PNAS, vol. 99, no. 22, pp. 14142-14146, 2002.; C. Gentil, G. Philippin and U. Bockelmann, "Signal enhancement in electronic detection of DNA hybridization," Phys. Rev. E, vol. 75, no. 1, p. 011926, 2007.).

According to the invention, as illustrated in FIG. 16, the combination of a small drift and a high signal amplitude greatly facilitates the detection of DNA hybridization in real time compared with the silicon devices according to the state of the art.

Of course, the invention is not limited to the examples which have just been described and numerous adjustments can be made to these examples without exceeding the scope of the invention.

For example, in a variant of the invention:
the method for using a device according to the invention or obtained by means of a production method according to the invention comprises a step of detecting an electrical activity of at least one biological cell on or above the conductive layer or the passivation layer, such as for example of at least one neuron, and/or
the first lithography of the layer 5 and the second lithography of the layer 6 can be two positive lithographies or two negative lithographies, and/or
after the deposition of the at least one electrode 7, the protective layer 4 can be preserved so as to preserve it between the layer 2 and the layer 8 (81, 82).

The invention claimed is:

1. A method for producing a device, comprising:
providing a conductive layer between a substrate and a protective layer;
depositing a first lithography resin layer above or on the protective layer such that the protective layer is comprised between the conductive layer and the first resin layer;
a first lithography comprising:
a) removing, in at least one removal area of the first lithography, the superimposition of the first resin layer, the protective layer and the conductive layer; and
b) preserving, in at least one preservation area of the first lithography, the superimposition of the first resin layer, the protective layer and the conductive layer; and
depositing, at least on the at least one preservation area of the first lithography, preferably on the at least one removal area and on the at least one preservation area of the first lithography, a second lithography resin layer without removing the first resin layer of the at least one preservation area of the first lithography; and
a second lithography comprising:
a) removing, in at least one removal area of the second lithography, the superimposition of the second resin, the first resin and the protective layer, but not the conductive layer; and
b) preserving, in at least one preservation area of the second lithography, the superimposition of the second resin, the first resin, the protective layer and the conductive layer.

2. The method according to claim 1, characterized in that the conductive layer comprises or consists of a two-dimensional conductor having a mobility greater than or equal to 1,000 $cm^2 \cdot V^{-1} s^{-1}$, preferably consisting of a layer of graphene, of silicene, of molybdenum disulfite ($MoS_2$), of germanene, of phosphorene, of stanene, or of borophene.

3. The method according to claim 1, characterized in that the first lithography is a positive or negative lithography and the second lithography is a negative or positive lithography respectively, the first resin layer and the second resin layer being constituted by one and the same resin compatible for a positive lithography and for a negative lithography.

4. The method according to claim 1, characterized in that the resin of the first resin layer and the resin of the second resin layer are arranged to react, during a lithography step:
to the same developer, and/or
to the same duration, power and wavelength of a preferably ultraviolet radiation.

5. The method according to claim 1, characterized in that the substrate comprises or consists of silicon and/or silicon oxide.

6. The method according to claim 1, characterized in that the protective layer comprises or consists of oxidized aluminium, preferably alumina $Al_2O_3$.

7. The method according to claim 1, characterized in that it moreover comprises, in the at least one removal area of the second lithography, depositing at least one electrode in electrical contact with the conductive layer.

8. The method according to claim 7, characterized in that it moreover comprises, after the deposition of the at least one electrode, removing, in the at least one preservation area of the second lithography, the superimposition of the second resin and the first resin, but not the conductive layer.

9. The method according to claim 8, characterized in that it moreover comprises, after the removal according to the preceding claim, depositing a passivation layer in contact with the conductive layer of the at least one preservation area of the second lithography and in contact with at least part of each electrode.

10. The method according to claim 9, characterized in that the passivation layer comprises a superimposition of two different materials.

11. The method according to claim 10, characterized in that the passivation layer comprises a superimposition:
of $Al_2O_3$ in contact with the conductive layer, then
of silicon oxide in contact with the $Al_2O_3$ of the passivation layer, such that the $Al_2O_3$ of the passivation layer is comprised between the conductive layer and the silicon oxide of the passivation layer.

12. The method according to claim 11, characterized in that the passivation layer has a breakdown field greater than or equal to $10^6$ $V \cdot m^{-1}$.

* * * * *